US011479823B2

(12) United States Patent
Allawi et al.

(10) Patent No.: US 11,479,823 B2
(45) Date of Patent: Oct. 25, 2022

(54) DETECTION OF LUNG NEOPLASIA BY AMPLIFICATION OF RNA SEQUENCES

(71) Applicant: Exact Sciences Corporation, Madison, WI (US)

(72) Inventors: Hatim Allawi, Middleton, WI (US); Graham P. Lidgard, Middleton, WI (US); Chateen Krueger, Fitchburg, WI (US); Michael W. Kaiser, Stoughton, WI (US); Tamara J. Sander, Mazomanie, WI (US)

(73) Assignee: Exact Sciences Corporation, Madison, WI (US)

( * ) Notice: Subject to any disclaimer, the term of this patent is extended or adjusted under 35 U.S.C. 154(b) by 0 days.

(21) Appl. No.: 17/078,924

(22) Filed: Oct. 23, 2020

(65) Prior Publication Data

US 2021/0155993 A1    May 27, 2021

Related U.S. Application Data

(63) Continuation of application No. 15/587,806, filed on May 5, 2017, now abandoned.

(60) Provisional application No. 62/332,419, filed on May 5, 2016.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,792,614 A | 7/1998 | Herman et al. |
| 5,846,717 A | 8/1998 | Western et al. |
| 5,849,481 A | 12/1998 | Brow et al. |
| 5,851,770 A | 12/1998 | Urdea et al. |
| 5,882,867 A | 3/1999 | Ullman et al. |
| 5,914,230 A | 3/1999 | Ullman et al. |
| 5,958,692 A | 6/1999 | Liu et al. |
| 5,965,408 A | 9/1999 | Cotton et al. |
| 5,985,557 A | 10/1999 | Short |
| 5,994,069 A | 11/1999 | Prudent et al. |
| 6,001,567 A | 11/1999 | Hall et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Western et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 2/2001 | Lizardi |
| 6,221,583 B1 | 4/2001 | Lizardi |
| 6,235,502 B1 | 5/2001 | Weissman et al. |
| 6,248,229 B1 | 6/2001 | Meade |
| 6,528,254 B1 | 3/2003 | Sorge |
| 6,630,333 B1 | 10/2003 | Hughes, Jr. |
| 6,872,816 B1 | 3/2005 | Hall et al. |
| 7,662,594 B2 | 2/2010 | Kong et al. |
| 8,206,904 B2 | 6/2012 | Allawi et al. |
| 8,361,720 B2 | 1/2013 | Oldham-Haltom et al. |
| 8,715,937 B2 | 5/2014 | Zou et al. |
| 8,916,344 B2 | 12/2014 | Zou et al. |
| 9,096,893 B2 | 8/2015 | Allawi et al. |
| 9,212,392 B2 | 12/2015 | Allawi et al. |
| 10,385,406 B2 | 8/2019 | Allawi et al. |
| 2007/0202525 A1 | 8/2007 | Quake et al. |
| 2009/0253142 A1 | 10/2009 | Allawi et al. |
| 2011/0052488 A1 | 3/2011 | Dennis, Jr. et al. |

(Continued)

FOREIGN PATENT DOCUMENTS

| | | |
|---|---|---|
| WO | WO 2002/070755 | 9/2002 |
| WO | WO 2005/023091 | 3/2005 |

(Continued)

OTHER PUBLICATIONS

Affymetrix probes from the Affymetrix U133 array, downloaded Dec. 4, 2018, 16 pages.

Ballabio, et al., Screening for steroid sulfatase (STS) gene deletions by multiplex DNA amplification, Human Genetics, 1990, 84(6): 571-573.

Barnay, Genetic disease detection and DNA amplification using cloned thermostable ligase, Proc. Natl. Acad. Sci USA, 1991, 88:189-93.

(Continued)

*Primary Examiner* — Katherine D Salmon

(74) *Attorney, Agent, or Firm* — Casimir Jones, S.C.; Mary Ann D. Brow

(57) ABSTRACT

Provided herein is technology for lung neoplasia screening and particularly, but not exclusively, to methods, compositions, and related uses for detecting the presence of lung cancer.

17 Claims, 8 Drawing Sheets

Specification includes a Sequence Listing.

(56) References Cited

U.S. PATENT DOCUMENTS

| | | | |
|---|---|---|---|
| 2014/0087382 A1 | 3/2014 | Allawi et al. | |
| 2014/0363471 A1* | 12/2014 | Hu | A61K 9/0019 |
| | | | 424/278.1 |
| 2017/0121757 A1 | 5/2017 | Lidgard et al. | |
| 2017/0335401 A1 | 11/2017 | Allawi et al. | |
| 2018/0245157 A1 | 8/2018 | Allawi et al. | |

FOREIGN PATENT DOCUMENTS

| | | |
|---|---|---|
| WO | WO 2006/050499 | 5/2006 |
| WO | WO 2017/075061 | 5/2017 |
| WO | WO 2017/192221 | 11/2017 |

OTHER PUBLICATIONS

Budd et al., Circulating tumor cells versus imaging-predicting overall survival in metastatic breast cancer. Clin Cancer Res. Nov. 1, 2006;12(21):6403-9.

Bustin, Absolute quantification of mRNA using real-time reverse transcription polymerase chain reaction assays, J. Molecular Endocrinology, 2000, 25:169-193.

Chamberlain et al., Deletion screening of the Duchenne muscular dystrophy locus via multiplex DNA amplification, Nucleic Acids Research, 1988, 16(23):11141-11156.

Cohen et al., Relationship of circulating tumor cells to tumor response, progression-free survival, and overall survival in patients with metastatic colorectal cancer. J Clin Oncol. Jul. 1, 2008;26(19):3213-21.

Cristofanilli et al., Circulating tumor cells, disease progression, and survival in metastatic breast cancer. N Engl J Med. Aug. 19, 2004;351(8):781-91.

Don et al., 'Touchdown' PCR to circumvent spurious priming during gene amplification, Nucleic Acids Research, 1991, 19(14):4008.

Guilfoyle et al., Ligation-mediated PCR amplification of specific fragments from a class-II restriction endonuclease total digest, Nucleic Acids Research, 1997, 25:1854-1858.

Hall et al., Sensitive detection of DNA polymorphisms by the serial invasive signal amplification reaction, PNAS, 2000, 97:8272.

Hayden et al., Multiplex-Ready PCR: A new method for multiplexed SSR and SNP genotyping, BMC Genomics, 2008, 9:80.

Hayes et al., Circulating tumor cells at each follow-up time point during therapy of metastatic breast cancer patients predict progression-free and overall survival. Clin Cancer Res. Jul. 15, 2006;12(14 Pt 1):4218-24.

Hecker et al., High and low annealing temperatures increase both specificity and yield in touchdown and stepdown PCR, Biotechniques, 1996, 20(3):478-485.

Higuchi et al., A general method of in vitro preparation and specific mutagenesis of DNA fragments: study of protein and DNA interactions, Nucleic Acids Research, 1988, 16(15):7351-7367.

Higuchi et al., Simultaneous amplification and detection of specific DNA sequences, Biotechnology, 1992, 10:413-417.

Higuchi et al., Kinetic PCR analysis: real-time monitoring of DNA amplification reactions, Biotechnology, 1993, 11:1026-1030.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection, Nucleic Acids Research, 1997, 25:1999-2004.

Lyamichev et al., Polymorphism identification and quantitative detection of genomic DNA by invasive cleavage of oligonucleotide probes, Nat. Biotech., 1999, 17:292-296.

Moreno et al., Circulating tumor cells predict survival in patients with metastatic prostate cancer. Urology. Apr. 2005;65(4):713-8.

Olivier, The Invader assay for SNP genotyping, Mutat Res. Jun. 3, 2005;573(1-2):103-10.

Orpana, Fluorescence resonance energy transfer (FRET) using ssDNA binding fluorescent dye, Biomol Eng. Apr. 2004;21(2):45-50.

Pantel et al., Detection, clinical relevance and specific biological properties of disseminating tumour cells. Nat Rev Cancer. May 2008;8(5):329-40.

Roux, Using mismatched primer-template pairs in touchdown PCR, Biotechniques, 1994, 16(5):812-814.

Schouten et al., Relative quantification of 40 nucleic acid sequences by multiplex ligation-dependent probe amplification, Nucleic Acids Research, 2002, 30(12): e57.

Selvin, Fluorescence resonance energy transfer, 1995, Methods Enzymol. 1995;246:300-34.

Shen et al., Multiple but dissectible functions of FEN-1 nucleases in nucleic acid processing, genome stability and diseases. Bioessays. Jul. 2005;27(7):717-29.

Stryer, Fluorescence energy transfer as a spectroscopic ruler, Annu Rev Biochem. 1978;47:819-46.

Triglia et al., A procedure for in vitro amplification of DNA segments that lie outside the boundaries of known sequences, Nucleic Acids Res., 1988, 16:8186.

Vogelstein et al., Digital PCR, PNAS, 1999, 96: 9236-41.

\* cited by examiner

FIG. 2

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 2 | 10 | 6 | 1,000,000 | 100% | 16 | 1,176,093 | -3.17 | 35.4 | 106.99% |
|  |  | 5 | 100,000 | 100% | 20 | 95,350 |  |  |  |
|  |  | 4 | 10,000 | 100% | 23 | 7,079 |  |  |  |
|  |  | 3 | 1,000 | 50% | 25 | 1,690 |  |  |  |
|  |  | 2 | 100 | 0% | NA | NA |  |  |  |
|  |  | 1 | 10 | 0% | NA | NA |  |  |  |
|  |  | 0 | 1 | 0% | NA | NA |  |  |  |
| MMLV (units) | RT time (min) | Log (RNA strands) | RNA Strands | Positivity (%) | Average Cp | Average Strands | Slope | Intercept | % Efficiency |
| 2 | 30 | 6 | 1,000,000 | 100% | 15.8 | 1429396 | -2.83 | 33.2 | 125.91% |
|  |  | 5 | 100,000 | 100% | 19.1 | 99202 |  |  |  |
|  |  | 4 | 10,000 | 100% | 22.6 | 5748 |  |  |  |
|  |  | 3 | 1,000 | 50% | 24.9 | 821 |  |  |  |
|  |  | 2 | 100 | 50% | 26.6 | 219 |  |  |  |
|  |  | 1 | 10 | 0% | NA | NA |  |  |  |
|  |  | 0 | 1 | 0% | NA | NA |  |  |  |
| MMLV (units) | RT time (min) | Log (RNA strands) | RNA Strands | Positivity (%) | Average Cp | Average Strands | Slope | Intercept | % Efficiency |
| 2 | 45 | 6 | 1,000,000 | 100% | 17.0 | 927417 | -3.40 | 37.3 | 96.78% |
|  |  | 5 | 100,000 | 100% | 20.0 | 116797 |  |  |  |
|  |  | 4 | 10,000 | 100% | 23.8 | 9517 |  |  |  |
|  |  | 3 | 1,000 | 0% | NA | NA |  |  |  |
|  |  | 2 | 100 | 0% | NA | NA |  |  |  |
|  |  | 1 | 10 | 0% | NA | NA |  |  |  |
|  |  | 0 | 1 | 0% | NA | NA |  |  |  |
| MMLV (units) | RT time (min) | Log (RNA strands) | RNA Strands | Positivity (%) | Average Cp | Average Strands | Slope | Intercept | % Efficiency |
| 4 | 10 | 6 | 1,000,000 | 100% | 16 | 1,007,096 | -3.62 | 37.3 | 88.87% |
|  |  | 5 | 100,000 | 100% | 19 | 116,764 |  |  |  |
|  |  | 4 | 10,000 | 100% | 23 | 7,981 |  |  |  |
|  |  | 3 | 1,000 | 50% | 26 | 1,392 |  |  |  |
|  |  | 2 | 100 | 0% | NA | NA |  |  |  |
|  |  | 1 | 10 | 0% | NA | NA |  |  |  |
|  |  | 0 | 1 | 0% | NA | NA |  |  |  |
| MMLV (units) | RT time (min) | Log (RNA strands) | RNA Strands | Positivity (%) | Average Cp | Average Strands | Slope | Intercept | % Efficiency |
| 4 | 30 | 6 | 1,000,000 | 100% | 15 | 1,136,170 | -3.25 | 34.9 | 103.28% |
|  |  | 5 | 100,000 | 100% | 18 | 127,887 |  |  |  |
|  |  | 4 | 10,000 | 100% | 23 | 5,661 |  |  |  |
|  |  | 3 | 1,000 | 100% | 25 | 1,067 |  |  |  |
|  |  | 2 | 100 | 50% | 28 | 182 |  |  |  |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 4 | 45 | 6 | 1,000,000 | 100% | 16.2 | 1142850 | -2.96 | 34.1 | 117.88% |
| | | 5 | 100,000 | 100% | 19.4 | 98545 | | | |
| | | 4 | 10,000 | 100% | 22.8 | 7365 | | | |
| | | 3 | 1,000 | 100% | 25.0 | 1270 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 10 | 6 | 1000000 | 100% | 14.8 | 876339 | -3.60 | 36.2 | 89.60% |
| | | 5 | 100000 | 100% | 17.9 | 119599 | | | |
| | | 4 | 10000 | 100% | 21.7 | 10739 | | | |
| | | 3 | 1000 | 100% | 25.5 | 918 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 30 | 6 | 1,000,000 | 100% | 14.0 | 1020824 | -3.27 | 33.7 | 102.09% |
| | | 5 | 100,000 | 100% | 17.1 | 117192 | | | |
| | | 4 | 10,000 | 100% | 21.1 | 6996 | | | |
| | | 3 | 1,000 | 100% | 23.6 | 1226 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 45 | 6 | 1,000,000 | 100% | 15.0 | 971743 | -3.22 | 34.3 | 104.61% |
| | | 5 | 100,000 | 100% | 18.0 | 115078 | | | |
| | | 4 | 10,000 | 100% | 21.7 | 8496 | | | |
| | | 3 | 1,000 | 100% | 24.5 | 1082 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | | 6 | 1,000,000 | 100% | 14.0 | 1522369 | | | |
| | | 5 | 100,000 | 100% | 17.4 | 101278 | | | |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 16 | 10 | 4 | 10,000 | 100% | 21.0 | 5331 | -2.84 | 31.6 | 124.98% |
| | | 3 | 1,000 | 100% | 23.3 | 834 | | | |
| | | 2 | 100 | 50% | 25.4 | 76 | | | |
| | | 1 | 10 | 50% | 28.3 | 7 | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 16 | 30 | 6 | 1,000,000 | 100% | 13.3 | 1162259 | -3.06 | 31.9 | 112.39% |
| | | 5 | 100,000 | 100% | 16.5 | 106440 | | | |
| | | 4 | 10,000 | 100% | 20.2 | 6802 | | | |
| | | 3 | 1,000 | 100% | 22.7 | 1019 | | | |
| | | 2 | 100 | 100% | 25.5 | 119 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 16 | 45 | 6 | 1,000,000 | 100% | 14.6 | 984355 | -3.17 | 33.6 | 106.78% |
| | | 5 | 100,000 | 100% | 17.7 | 103465 | | | |
| | | 4 | 10,000 | 100% | 20.9 | 9870 | | | |
| | | 3 | 1,000 | 0% | NA | NA | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 32 | 10 | 6 | 1,000,000 | 100% | 15 | 1,244,785 | -3.01 | 32.9 | 114.78% |
| | | 5 | 100,000 | 100% | 18 | 101,820 | | | |
| | | 4 | 10,000 | 100% | 21 | 7,079 | | | |
| | | 3 | 1,000 | 100% | 24 | 876 | | | |
| | | 2 | 100 | 50% | 26 | 188 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 32 | 30 | 6 | 1,000,000 | 100% | 13.4 | 1166910 | -2.89 | 30.9 | 121.94% |
| | | 5 | 100,000 | 100% | 16.5 | 94672 | | | |
| | | 4 | 10,000 | 100% | 19.8 | 7302 | | | |
| | | 3 | 1,000 | 100% | 21.9 | 1306 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 32 | 45 | 6 | 1,000,000 | 100% | 14.8 | 941782 | | | |
| | | 5 | 100,000 | 100% | 17.6 | 107487 | | | |
| | | 4 | 10,000 | 100% | 20.7 | 10662 | | | |
| | | 3 | 1,000 | 100% | 24.0 | 944 | -3.07 | 33.1 | 111.60% |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 10 | 6 | 1,000,000 | 100% | 15.0 | 682439 | | | |
| | | 5 | 100,000 | 100% | 17.8 | 125812 | | | |
| | | 4 | 10,000 | 100% | 20.8 | 19833 | | | |
| | | 3 | 1,000 | 100% | 26.5 | 806 | -3.77 | 37.0 | 84.15% |
| | | 2 | 100 | 50% | 29.5 | 96 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 30 | 6 | 1,000,000 | 100% | 14.4 | 607851 | | | |
| | | 5 | 100,000 | 100% | 17.2 | 127785 | | | |
| | | 4 | 10,000 | 100% | 20.6 | 19204 | | | |
| | | 3 | 1,000 | 100% | 26.0 | 1174 | -4.17 | 38.4 | 73.80% |
| | | 2 | 100 | 100% | 30.8 | 148 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 45 | 6 | 1,000,000 | 100% | 15.0 | 582944 | | | |
| | | 5 | 100,000 | 100% | 17.6 | 140634 | | | |
| | | 4 | 10,000 | 100% | 20.7 | 25564 | | | |
| | | 3 | 1,000 | 100% | 28.0 | 2324 | -4.21 | 39.2 | 72.89% |
| | | 2 | 100 | 0% | NA | NA | | | |
| | | 1 | 10 | 0% | NA | NA | | | |
| | | 0 | 1 | 0% | NA | NA | | | |

FIG. 3
A.
| LRG-1 RNA | | Cp | | Calc. Strands/Rxn | |
|---|---|---|---|---|---|
| Dilution | Strand/Rxn | Ave | %CV | Ave | %CV |
| A | 100,000 | 9.7 | 0.5% | 106,229 | 3.3% |
| B | 10,000 | 13.1 | 0.2% | 9,695 | 1.7% |
| C | 1,000 | 16.4 | 0.2% | 989 | 2.5% |
| D | 100 | 19.9 | 0.4% | 88 | 5.7% |
| E | 10 | 22.8 | 2.7% | 12 | 41.0% |
B.
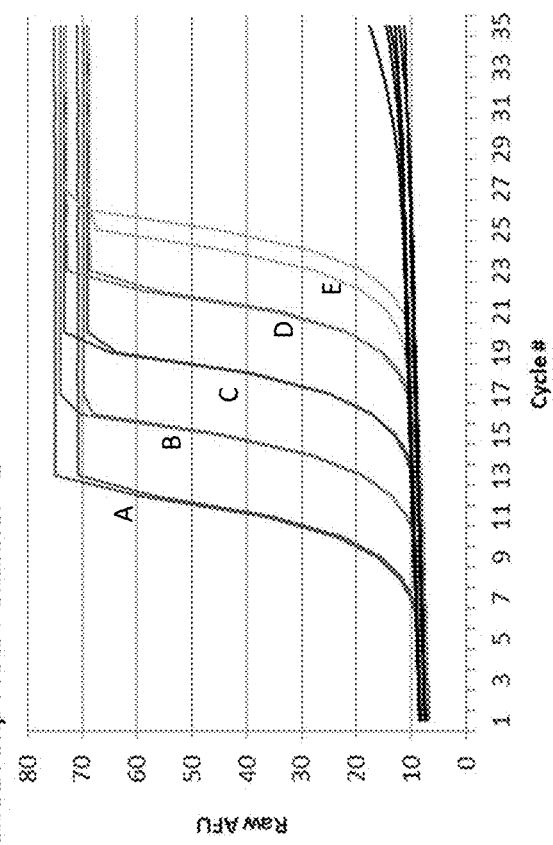
C.
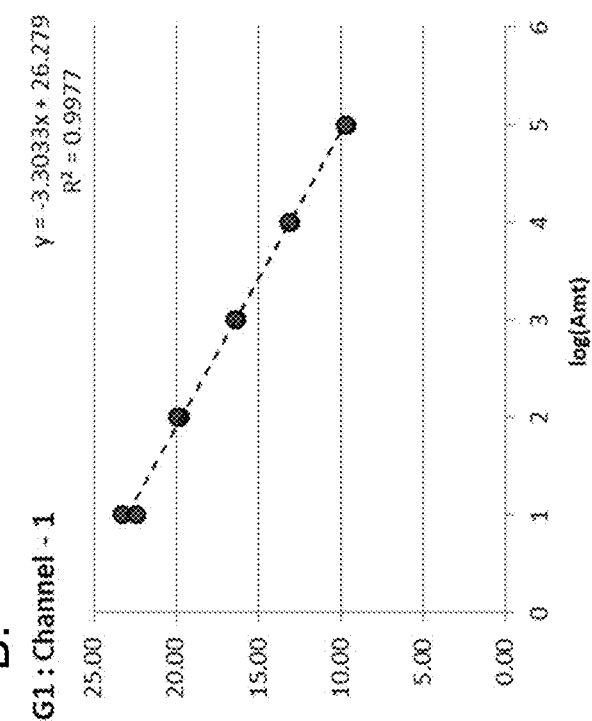

FIG. 5
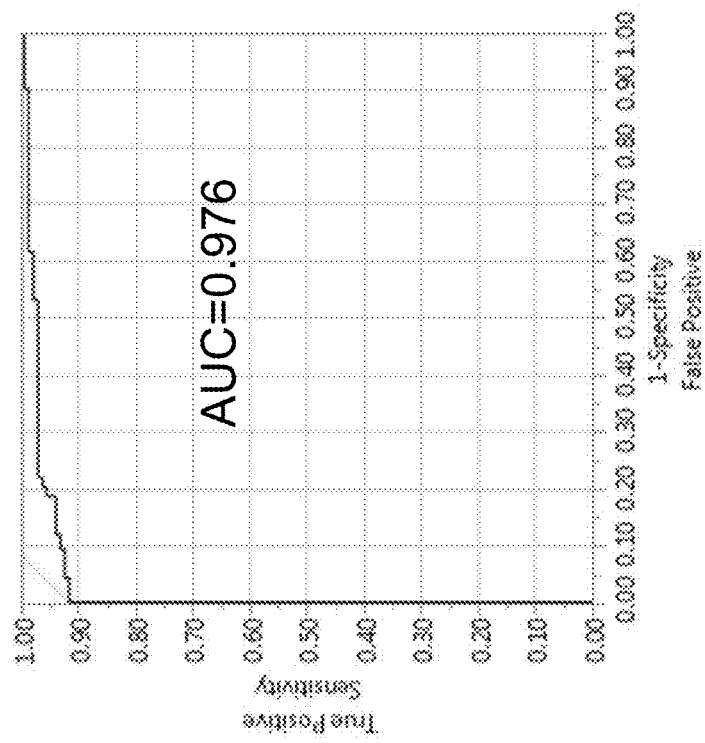
B.
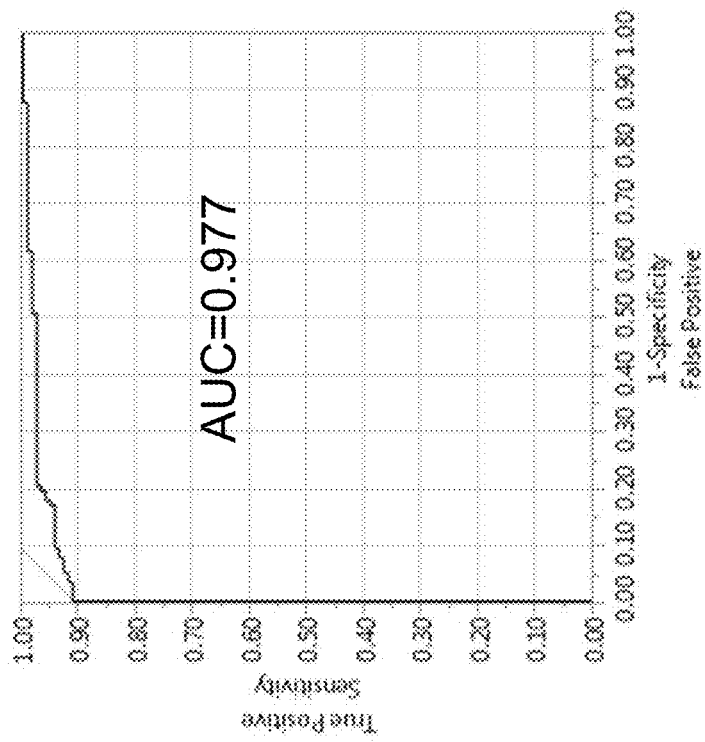
A.

SEQUENCE LISTING

<160> NUMBER OF SEQ ID NOS: 36

<210> SEQ ID NO 1
<211> LENGTH: 24
<212> TYPE: DNA
<213> ORGANISM: Artificial sequence
<220> FEATURE:
<223> OTHER INFORMATION: Synthetic DNA Primer/Probe

<400> SEQUENCE: 1
ggacactgag aagaaagacc agtc                                          24

<210> SEQ ID NO 2
<211> LENGTH: 21

```
<212> TYPE: DNA
<213> ORGANISM: Artificial sequence
<220> FEATURE:
<223> OTHER INFORMATION: Synthetic DNA Primer/Probe

<400> SEQUENCE: 2
gggagcttgt tgaaaaggc a                                           21

<210> SEQ ID NO 3
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 3
ccacggacgc taagacagag g                                          21

<210> SEQ ID NO 4
<211> LENGTH: 18
<212> TYPE: DNA
<213> ORGANISM: Artificial sequence
<220> FEATURE:
<223> OTHER INFORMATION: Synthetic DNA Primer/Probe

<400> SEQUENCE: 4
ctgcaaccac gggaactt                                              18

<210> SEQ ID NO 5
<211> LENGTH: 18
<212> TYPE: DNA
<213> ORGANISM: Artificial sequence
<220> FEATURE:
<223> OTHER INFORMATION: Synthetic DNA Primer/Probe

<400> SEQUENCE: 5
gaggtggagg tcctgctc                                              18

<210> SEQ ID NO 6
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 6
gacgcggagt cgaggtatgc c                                          21

<210> SEQ ID NO 7
<211> LENGTH: 23
<212> TYPE: DNA
<213> ORGANISM: Artificial sequence
<220> FEATURE:
<223> OTHER INFORMATION: Synthetic DNA Primer/Probe

<400> SEQUENCE: 7
cttcaactgc atttggctct ttg                                        23

<210> SEQ ID NO 8
<211> LENGTH: 17
<212> TYPE: DNA
<213> ORGANISM: Artificial sequence
<220> FEATURE:
<223> OTHER INFORMATION: Synthetic DNA Primer/Probe

<400> SEQUENCE: 8
```

-continued

```
tgtggcctgg atgtcgt                                          17

<210> SEQ ID NO 9
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 9
ccacggacgg ttggattgtc c                                     21

<210> SEQ ID NO 10
<211> LENGTH: 23
<212> TYPE: DNA
<213> ORGANISM: Artificial sequence
<220> FEATURE:
<223> OTHER INFORMATION: Synthetic DNA Primer/Probe

<400> SEQUENCE: 10
tggagatttg tcctgtctgg atc                                   23

<210> SEQ ID NO 11
<211> LENGTH: 20
<212> TYPE: DNA
<213> ORGANISM: Artificial sequence
<220> FEATURE:
<223> OTHER INFORMATION: Synthetic DNA Primer/Probe

<400> SEQUENCE: 11
cttggagagg atgttccggt                                       20

<210> SEQ ID NO 12
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 12
ccacggacgc ttacagcttc a                                     21

<210> SEQ ID NO 13
<211> LENGTH: 18
<212> TYPE: DNA
<213> ORGANISM: Artificial sequence
<220> FEATURE:
<223> OTHER INFORMATION: Synthetic DNA Primer/Probe

<400> SEQUENCE: 13
agggagcatc tgcaggtc                                         18

<210> SEQ ID NO 14
<211> LENGTH: 22
<212> TYPE: DNA
<213> ORGANISM: Artificial sequence
<220> FEATURE:
<223> OTHER INFORMATION: Synthetic DNA Primer/Probe

<400> SEQUENCE: 14
cctgttcctg gctatgagct tc                                    22

<210> SEQ ID NO 15
<211> LENGTH: 20
<212> TYPE: DNA
<213> ORGANISM: Artificial sequence
```

```
<220> FEATURE:
<223> OTHER INFORMATION: Synthetic DNA Primer/Probe

<400> SEQUENCE: 15
cgccgaggca agggccgaag                                                    20

<210> SEQ ID NO 16
<211> LENGTH: 18
<212> TYPE: DNA
<213> ORGANISM: Artificial sequence
<220> FEATURE:
<223> OTHER INFORMATION: Synthetic DNA Primer/Probe

<400> SEQUENCE: 16
gagcagacag cgaccaaa                                                      18

<210> SEQ ID NO 17
<211> LENGTH: 25
<212> TYPE: DNA
<213> ORGANISM: Artificial sequence
<220> FEATURE:
<223> OTHER INFORMATION: Synthetic DNA Primer/Probe

<400> SEQUENCE: 17
caggaacaga gttctagaaa catgg                                              25

<210> SEQ ID NO 18
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 18
ccacggacga agcccaggg g                                                   21

<210> SEQ ID NO 19
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 19
agaggagcac caaggagaag a                                                  21

<210> SEQ ID NO 20
<211> LENGTH: 19
<212> TYPE: DNA
<213> ORGANISM: Artificial sequence
<220> FEATURE:
<223> OTHER INFORMATION: Synthetic DNA Primer/Probe

<400> SEQUENCE: 20
ggcaaaagct gggcaatgg                                                     19

<210> SEQ ID NO 21
<211> LENGTH: 20
<212> TYPE: DNA
<213> ORGANISM: Artificial sequence
<220> FEATURE:
<223> OTHER INFORMATION: Synthetic DNA Primer/Probe

<400> SEQUENCE: 21
cgccgaggat ctgcctgtgg                                                    20
```

<210> SEQ ID NO 22
<211> LENGTH: 22
<212> TYPE: DNA
<213> ORGANISM: Artificial sequence
<220> FEATURE:
<223> OTHER INFORMATION: Synthetic DNA Primer/Probe

<400> SEQUENCE: 22
gtcatcgact acttccagaa cc                                              22

<210> SEQ ID NO 23
<211> LENGTH: 18
<212> TYPE: DNA
<213> ORGANISM: Artificial sequence
<220> FEATURE:
<223> OTHER INFORMATION: Synthetic DNA Primer/Probe

<400> SEQUENCE: 23
aggtgcatac agatgccg                                                   18

<210> SEQ ID NO 24
<211> LENGTH: 20
<212> TYPE: DNA
<213> ORGANISM: Artificial sequence
<220> FEATURE:
<223> OTHER INFORMATION: Synthetic DNA Primer/Probe

<400> SEQUENCE: 24
cgccgaggca gactgactca                                                 20

<210> SEQ ID NO 25
<211> LENGTH: 17
<212> TYPE: DNA
<213> ORGANISM: Artificial sequence
<220> FEATURE:
<223> OTHER INFORMATION: Synthetic DNA Primer/Probe

<400> SEQUENCE: 25
cccaggtgct gggaagg                                                    17

<210> SEQ ID NO 26
<211> LENGTH: 20
<212> TYPE: DNA
<213> ORGANISM: Artificial sequence
<220> FEATURE:
<223> OTHER INFORMATION: Synthetic DNA Primer/Probe

<400> SEQUENCE: 26
actgatgcag ctcttgcaga                                                 20

<210> SEQ ID NO 27
<211> LENGTH: 21
<212> TYPE: DNA
<213> ORGANISM: Artificial sequence
<220> FEATURE:
<223> OTHER INFORMATION: Synthetic DNA Primer/Probe

<400> SEQUENCE: 27
ccacggacgg gaaatgcgcg a                                               21

<210> SEQ ID NO 28
<211> LENGTH: 2867
<212> TYPE: DNA
<213> ORGANISM: Homo sapiens

<400> SEQUENCE: 28

```
caggggtggc agccaactgc aggtgcccaa gaacttggca cttctcagtt ccatctaaag        60
gggcacatct cccttctggg tgtcacgttt tcagccaaac atctaaaaga acttcatcat       120
caagatgtct gatgatattg actggttacg cagccacagg ggtgtgtgca aggtagatct       180
ctacaaccca gaaggacagc aagatcagga ccggaaagtg atatgctttg tcgatgtgtc       240
caccctgaat gtagaagata aagattacaa ggatgctgct agttccagct cagaaggcaa       300
cttaaacctg ggaagtctgg aagaaaaaga gattatcgtg atcaaggaca ctgagaagaa       360
agaccagtct aagacagagg gatctgtatg ccttttcaaa caagctccct ctgatcctgt       420
aagtgtcctc aactggcttc tcagtgatct ccagaagtat gccttgggtt tccaacatgc       480
actgagcccc tcaacctcta cctgtaaaca taaagtagga gacacagagg gcgaatatca       540
cagagcatcc tctgagaact gctacagtgt ctatgccgat caagtgaaca tagattattt       600
gatgaacaga cctcaaaacc tacgtctaga aatgacagca gctaaaaaca ccaacaataa       660
tcaaagtcct tcagctcctc cagccaaacc tcctagcact cagagagcag tcatttcccc       720
tgatggagaa tgttctatag atgaccttc cttctacgtc aaccgactat cttctctggt       780
aatccagatg gcccataagg aaatcaagga gaagttggaa ggtaaaagca atgccttca       840 tcattcaatc tgtccatccc ctgggaacaa agagagaatc agtccccgaa ctcctgcgag       900
caagattgct tctgaaatgg cctatgaagc tgtggaactg acagctgcag aaatgcgtgg       960
cactggagag gagtccaggg aaggtggcca gaaaagcttt ctatatagcg aattatccaa      1020
caagagcaaa agtggagaca acagatgtc cagagagag agcaaagaat ttgcagattc       1080
catcagcaag gggctcatgg tttatgcaaa tcaggtggca tctgacatga tggtctctct      1140
catgaagacc ttgaaagtgc acagctctgg gaagccaatt ccagcatctg tggtcctgaa      1200
gagggtgttg ctaaggcaca ccaaggagat tgtgtccgat tgattgatt cttgcatgaa       1260 gaacctgcat aatattactg gggtcctgat gactgactca gactttgtct cagctgtcaa      1320
gagaaatctg ttcaaccagt ggaaacaaaa tgctacagac atcatggagg ccatgctgaa      1380
gcgcttggtc agtgccctta taggtgagga aagggagact aagtctcaga gtctgtcata      1440 tgcatctta aaagctgggt cccatgatcc caaatgcagg aatcagagtc ttgaattctc       1500
caccatgaaa gctgaaatga agagaggga caaaggcaaa atgaaatcag acccatgcaa      1560
gtcactgact agtgctgaga agtcggtga acacattctc aaagagggcc taaccatctg       1620
gaaccaaaag caaggaaact catgcaaggt ggctaccaaa gcatgcagca ataaagatga      1680
gaaaggagaa aagatcaatg cttccacaga ttcactggcc aaggacctga ttgtctctgc      1740
ccttaagctg atccagtacc atctgaccca gcagactaag ggcaaagata catgtgaaga      1800
agactgtcct ggttccacca tgggctatat ggctcagagt actcaatatg aaaagtgtgg      1860
aggtggccaa agtgccaaag cactttcagt gaaacaacta gaatctcaca gagcccctgg      1920
accatccacc tgtcaaaagg agaaccaaca cctggactcc cagaaaatgg atatgtcaaa      1980
catcgttcta atgctgattc agaaactgct taatgagaac cccttcaaat gtgaggatcc      2040
atgcgaaggt gagaacaagt gttctgagcc cagggcaagc aaagcagctt ccatgtccaa      2100
cagatctgac aaagcggaag aacaatgcca ggagcatcaa gaacttgact gtaccagtgg      2160
gatgaagcaa gcgaacgggc aatttataga taaactagta aatctgtga tgaagctctg       2220 ccttatcatg gctaagtata gcaacgatgg ggcagccctt gctgagttgg aagaacaagc      2280
agcctcggca aataagccca atttcagggg caccagatgc attcacagtg gtgcaatgcc      2340
```

| | |
|---|---|
| acagaactat caagactctc ttggacatga agtaattgtc aataatcagt gctctacaaa | 2400 |
| tagcttgcag aagcagctcc aggctgtcct gcagtggatt gcagcctccc agtttaacgt | 2460 |
| gcccatgctc tacttcatgg gagataagga tggacaactg gaaaagcttc ctcaggtttc | 2520 |
| agctaaagca gcagagaagg ggtacagtgt aggaggtctt cttcaagagg tcatgaagtt | 2580 |
| tgccaaggaa cggcaaccag atgaagctgt gggaaaggtg gccaggaaac agttgctgga | 2640 |
| ctggctgctc gctaacctgt gagctgatcc ttgactcctc ttcatcttag ccccctagc | 2700 |
| agcattccat cccagccaga gcaccccac catcaggcca gtcaactgca caatacacaa | 2760 |
| ctgtatttcc caatacactt gagcagttgc ctgtgaatgt aagaggtgtc aacaaactgg | 2820 |
| gaaataaaat aaaaaaaat aataaaaaaa aaaaaaaaa aaaaaa | 2867 |

<210> SEQ ID NO 29
<211> LENGTH: 4198
<212> TYPE: DNA
<213> ORGANISM: Homo sapiens

<400> SEQUENCE: 29

| | |
|---|---|
| aatccgggtc ggccgcaaac gtgccgcagg cctaggcccc gcccagtgcc ccgcccctcc | 60 |
| cccaacacac acacacacac acacacacac acacaccccca acacacacac acaccccca | 120 |
| acacacacac acacacacac acacacacac acacacacac acacacacac acacacagcg | 180 |
| ggatggccga gcgccgcacg cgtagcacgc cgggactagc tatccagcct cccagcagcc | 240 |
| tctgcgacgg gcgcggtgcg taagtacctc gccggtggtg gccgttctcc gtaagatggc | 300 |
| ggaccggcgc cggcagcgcg cttcgcaaga caccgaggac gaggaatctg gtgcttcggg | 360 |
| ctccgacagc ggcggctccc cgttgcgggg aggcgggagc tgcagcggta gcgccggagg | 420 |
| cggcggcagc ggctctctgc cttcacacgc cggaggccga accggggccc ttcatctgcg | 480 |
| gcgggtggag agcgggggcg ccaagagtgc tgaggagtcg gagtgtgaga gtgaagatgg | 540 |
| cattgaaggt gatgctgttc tctcggatta tgaaagtgca aagactcgg aaggtgaaga | 600 |
| aggtgaatac agtgaagagg aaaactccaa agtggagctg aaatcagaag ctaatgatgc | 660 |
| tgttaattct tcaacaaaag aagagaaggg agaagaaaag cctgacacca aaagcactgt | 720 |
| gactggagag aggcaaagtg gggacggaca ggagagcaca gagcctgtgg agaacaaagt | 780 |
| gggtaaaaag ggccctaagc atttggatga tgatgaagat cggaagaatc cagcatacat | 840 |
| acctcggaaa gggctcttct ttgagcatga tcttcgaggg caaactcagg aggaggaagt | 900 |
| cagacccaag gggcgtcagc gaaagctatg gaaggatgag ggtcgctggg agcatgacaa | 960 |
| gttccgggaa gatgagcagg ccccaaagtc ccgacaggag ctcattgctc tttatggtta | 1020 |
| tgacattcgc tcagctcata atcctgatga catcaaacct cgaagaatcc ggaaaccccg | 1080 |
| atatgggagt cctccacaaa gagatccaaa ctggaacggt gagcggctaa caagtctca | 1140 |
| tcgccaccag ggtcttgggg gcaccctacc accaaggaca tttattaaca ggaatgctgc | 1200 |
| aggtaccggc cgtatgtctg cacccaggaa ttattctcga tctgggggct tcaaggaagg | 1260 |
| tcgtgctggt tttaggcctg tggaagctgg tgggcagcat ggtggccggt ctggtgagac | 1320 |
| tgttaagcat gagattagtt accggtcacg gcgcctagag cagacttctg tgagggatcc | 1380 |
| atctccagaa gcagatgctc cagtgcttgg cagtcctgag aaggaagagg cagcctcaga | 1440 |
| gccaccagct gctgctcctg atgctgcacc accacccct gataggccca ttgagaagaa | 1500 |
| atcctattcc cgggcaagaa gaactcgaac caaagttgga gatgcagtca agcttgcaga | 1560 |
| ggaggtgccc cctcctcctg aaggactgat tccagcacct ccagtcccag aaaccacccc | 1620 |

```
aactccacct actaagactg ggacctggga agctccggtg gattctagta caagtggact    1680
tgagcaagat gtggcacaac taaatatagc agaacagaat tggagtccgg ggcagccttc    1740
tttcctgcaa ccacgggaac ttcgaggtat gcccaaccat atacacatgg gagcaggacc    1800
tccacctcag tttaaccgga tggaagaaat gggtgtccag ggtggtcgag ccaaacgcta    1860
ttcatcccag cggcaaagac ctgtgccaga gccccccgcc cctccagtgc atatcagtat    1920
catggaggga cattactatg atccactgca gttccaggga ccaatctata cccatggtga    1980
cagccctgcc ccgctgcctc cacagggcat gcttgtgcag ccaggaatga accttcccca    2040
cccaggttta catccccacc agacaccagc tcctctgccc aatccaggcc tctatccccc    2100
accagtgtcc atgtctccag acagccacc acctcagcag ttgcttgctc ctacttactt    2160
ttctgctcca ggcgtcatga actttggtaa tcccagttac ccttatgctc caggggcact    2220
gcctccccca ccaccgcctc atctgtatcc taatacacag gccccatcac aggtatatgg    2280
aggagtgacc tactataacc ccgcccagca gcaggtgcag ccaaagccct ccccaccccg    2340
gaggactccc cagccagtca ccatcaagcc ccctccacct gaggttgtaa gcaggggttc    2400
cagttaatac aagtttctga atattttaaa tcttaacatc atataaaaag cagcagaggt    2460
gagaactcag aagagaaata cagctggcta tctactacca gaagggcttc aaagatatag    2520
ggtgtggctc ctaccagcaa acagctgaaa gaggaggacc cctgccttcc tctgaggaca    2580
ggctctagag agagggagaa acaagtggac ctcgtcccat cttcactctt cacttgagtt    2640
ggctgtgttc gggggagcag agagagccag acagccccaa gcttctgagt ctagatacag    2700
aagcccatgt cttctgctgt tcttcacttc tgggaaattg aagtgtcttc tgttcccaag    2760
gaagctcctt cctgtttgtt ttgttttcta agatgttcat ttttaaagcc tggcttctta    2820
tccttaatat tattttaatt ttttctcttt gtttctgttt cttgctctct ctccctgcct    2880
ttaaatgaaa caagtctagt cttctggttt tctagcccct ctggattccc ttttgactct    2940
tccgtgcatc ccagataatg gagaatgtat cagccagcct tccccaccaa gtctaaaaag    3000
acctggcctt tcacttttag ttggcatttg ttatcctctt gtatacttgt attcccttaa    3060
ctctaaccct gtggaagcat ggctgtctgc acagagggtc ccattgtgca gaaaagctca    3120
gagtaggtgg gtaggagccc ttctctttga cttaggtttt taggagtctg agcatccatc    3180
aatacctgta ctatgatggg cttctgttct ctgctgaggg ccaatacccct actgtgggga    3240 gagatggcac accagatgct tttgtgagaa agggatggtg gagtgagagc ctttgccttt    3300
aggggtgtgt attcacatag tcctcagggc tcagtctttt gaggtaagtg gaattagagg    3360
gccttgcttc tcttctttcc attcttcttg ctacaccct tttccagttg ctgtggacca    3420
atgcatctct ttaaaggcaa atattatcca gcaagcagtc taccctgtcc tttgcaattg    3480
ctcttctcca cgtctttcct gctacaagtg ttttagatgt tactacctta ttttccccga    3540
attctatttt tgtccttgca gacagaatat aaaaactcct gggcttaagg cctaaggaag    3600
ccagtcacct tctgggcaag ggctcctatc tttcctccct atccatggca ctaaaccact    3660
tctctgctgc ctctgtggaa gagattccta ttactgcagt acatacgtct gccagggta    3720 acctggccac tgtccctgtc cttctacaga acctgagggc aaagatggtg gctgtgtctc    3780
tccccggtaa tgtcactgtt tttattcctt ccatctagca gctggcctaa tcactctgag    3840
tcacaggtgt gggatggaga gtggggagag gcacttaatc tgtaaccccc aaggaggaaa    3900
taactaagag attcttctag gggtagctgg tggttgtgcc ttttgtaggc tgttcccttt    3960
```

```
gccttaaacc tgaagatgtc tcctcaagcc tgtgggcagc atgcccagat tcccagacct    4020
taagacactg tgagagttgt ctctgttggt ccactgtgtt tagttgcaag gattttccca    4080
tgtgtggtgg tgttttttgt tactgtttta aagggtgccc atttgtgatc agcattgtga    4140
cttggagata ataaaattta gactataaac ttggctccct aaaaaaaaaa aaaaaaa      4198

<210> SEQ ID NO 30
<211> LENGTH: 3287
<212> TYPE: DNA
<213> ORGANISM: Homo sapiens

<400> SEQUENCE: 30
gacaggagga aacgcagcgc cagcagcatc tcatctaccc tccttgacac ctccccgtgg      60
ctccagccag accctagagg tcagccttgc ggaccaacag gaggactccc agctttccct     120
tttcaagagg tccccagaca ccggccaccc tcttccagcc cctgcggcca gtgcaaggag     180
gcaccaatgc tctgaggctg tcgcgtggtg cagcgtcgag catcctcgcc gaggtccttt     240
ctgctgcctg tcccgcctca ccccgctcca tcacaccagc tggccctctt tgcttccttt     300
tcccagaatc gttaagcccc gactcccact agcacctcgt accaacctcg ccccacccca     360
tcctcctgcc ttcccgcgct ccggtgtccc ccgctgccat gagctccccc atcagcaaga     420
gccgctcgct tgccgccttc ctgcagcagc tgcgcagtcc gaggcagccc ccgagactgg     480
tgacatctac ggcgtacacg tcccctcagc cgcgagaggt gccagtctgc ccgctgacag     540
ctggtggcga gactcagaac gcggccgccc tgccgggccc caccagctgg ccactgctgg     600
gcagcctgct gcagattctc tggaaagggg gtctcaagaa acagcacgac accctggtgg     660
agtaccacaa gaagtatggc aagatttttc gcatgaagtt gggttccttt gagtcggtgc     720
acctgggctc gccatgcctg ctggaagcgc tgtaccgcac cgagagcgcg tacccgcagc     780
ggctggagat caaaccgtgg aaggcctatc gcgactaccg caaagaaggc tacgggctgc     840
tgatcctgga aggggaagac tggcagcggg tccgagtgc ctttcaaaag aaactaatga     900
aaccagggga agtgatgaag ctggacaaca aaatcaatga ggtcttggcc gattttatgg     960
gcagaataga tgagctctgt gatgaaagag gccacgttga agacttgtac agcgaactga    1020
acaaatggtc gtttgaaagt atctgcctcg tgttgtatga agagatttg ggcttctcc      1080 agaagaatgc aggggatgaa gctgtgaact tcatcatggc catcaaaaca atgatgagca    1140
cgtttgggag gatgatggtc actccagtcg agctgcacaa gagcctcaac accaaggtct    1200
ggcaggacca cactctggcc tgggacacca ttttcaaatc agtcaaagct tgtatcgaca    1260
accggttaga gaagtattct cagcagccta gtgcagattt cctttgtgac atttatcacc    1320
agaatcggct ttcaaagaaa gaattgtatg ctgctgtcac agagctccag ctggctgcgg    1380
tggaaacgac agcaaacagt ctaatgtgga ttctctacaa tttatcccgt aatccccaag    1440
tgcaacaaaa gcttcttaag gaaattcaaa gtgtattacc tgagaatcag gtgccacggg    1500
cagaagattt gaggaatatg ccgtatttaa aagcctgtct gaaagaatct atgaggctta    1560
cgccgagtgt accatttaca actcggactc ttgacaaggc aacagttctg ggtgaatatg    1620
ctttacccaa aggaacagtg ctcatgctaa atacccaggt gttgggatcc agtgaagaca    1680 atttgaaga ttcaagtcag tttagacctg aacgttggct tcaggagaag gaaaaaatta     1740 atcctttgc gcatcttcca tttggcgttg gaaaagaat gtgcattggt cgccgattag      1800
cagagcttca actgcatttg gctctttgtt ggattgtccg caaatacgac atccaggcca    1860
cagacaatga gcctgttgag atgctacact caggcaccct ggtgcccagc cgggaactcc    1920
```

-continued

| | |
|---|---|
| ccatcgcgtt tgccagcga taatacgcct cagatggtgg tatttgctaa catcatatcc | 1980 |
| aactcaggga agcggactga gtgctgggat ccaaggcatt ctacagggtt cactgctggt | 2040 |
| ttacacttca cctgtgtcag caccatcttc aggtgcttag aatggcctgg gagcctgttc | 2100 |
| tgtcttgcat cttccatgac atgaaaggga ggctggcact tgtcagtcag gtagaggtta | 2160 |
| caaaccgttt caggccctgc ctaccacatt cactgtttga atctttaatt cccaagaata | 2220 |
| agtttacatt tcacaatgaa tgacctacaa cagctaaatt ttctggggct gggagtaata | 2280 |
| ctgacaatcc atttactgta gctctgctta atgtactact taggaaaatg tccctgctta | 2340 |
| ataatgtaag ccaagctaaa tgatggttaa agttatcagg cctcccatga aattgcgttc | 2400 |
| ttcctgcatt gaaataaaaa cattattggg aaactagaga acacctctat ttttaaaagg | 2460 |
| actttaacga agtcaaacaa cttataagac tagtgattca ctggggcatt attttgttag | 2520 |
| aggaccttaa aattgtttat ttttaaatg tgattccttt atggcattag ggtaaagatg | 2580 |
| aagcaataat ttttaaattg tgtatgtgca tatgaagcac agacatgcat gtgtgtgtgt | 2640 |
| gtctgtgtgt gtgtgtccgt gtatgtgtgt gtgggttcta atggtaattt gcctcagtca | 2700 |
| ttttttttaat atttgcagta cttgatttag gatctgtggt gcagggcaat gtttcaaagt | 2760 |
| ttagtcacag cttaaaaaca ttcagtgtga ctttaatatt ataaaatgat ttcccatgcc | 2820 |
| ataattttc tgtctattaa atgggacaag tgtaaagcat gcaaaagtta gagatctgtt | 2880 |
| atataacatt tgttttgtga tttgaactcc taggaaaaat atgatttcat aaatgtaaaa | 2940 |
| tgcacagaaa tgcatgcaat acttataaga cttaaaaatt gtgtttacag atggtttatt | 3000 |
| tgtgcatatt tttactactg cttttcctaa atgcatactg tatataattc tgtgtatttg | 3060 |
| ataaatattt cttcctacat tatattttta gaatatttca gaaatataca tttatgtctt | 3120 |
| tatattgtaa taaatatgta catatctagg tatatgcttt ctctctgctg tgaaattatt | 3180 |
| tttagaatta taaattcacg tcttgtcaga tttcatctgt ataccttcaa attctctgaa | 3240 |
| agtaaaaata aaagttttta aatattaaaa aaaaaaaaa aaaaaa | 3287 |

<210> SEQ ID NO 31
<211> LENGTH: 3829
<212> TYPE: DNA
<213> ORGANISM: Homo sapiens

<400> SEQUENCE: 31

| | |
|---|---|
| aggaaatatc ccatggctga ctgtgccaag gaggtgtctg agccagccct cccggcccga | 60 |
| gggcagggca ggtggccctg agagataagc caatcccgca gctgcagatg aggagttctg | 120 |
| agaagcattg ctcaggacag cggtaaatca cttcttggag gtgccctgca cgccggtcct | 180 |
| gggagcaggc ggcctcccgg gggtgcggga gccccactcc tccgtggtgt gttccatttg | 240 |
| cttcccacat ctggaggagc tgacgtgcca gcctccccca gcaccaccca gggacgggag | 300 |
| gcatgagccg tcaaggcac ctgggcaaaa tccggaagcg tctggaagat gtcaagagcc | 360 |
| agtgggtccg gccagccagg gctgactta gtgacaacga gagtgcccgg ctggccacgg | 420 |
| acgccctctt ggatgggggt tctgaagcct actggcgggt gctcagccag gaaggcgagg | 480 |
| tggacttctt gtcctcggtg gaggcccagt acatccaggc ccaggccagg gagccccgt | 540 |
| gtccccaga caccctggga ggggcggaag caggccctaa gggactggac tccagctccc | 600 |
| tacagtccgg cacctacttc cctgtggcct cagagggcag cgagccggcc ctactgcaca | 660 |
| gctgggcctc agctgagaag ccctacctga aggaaaaatc cagcgccact gtgtacttcc | 720 |

| | |
|---|---|
| agaccgtcaa gcacaacaac atcagagacc tcgtccgccg ctgcatcacc cggactagcc | 780 |
| agaacatttc catccggagt gtggaaggag agatatactg tgccaagtca ggcaggaaat | 840 |
| tcgctggcca aatccgggag aagttcatca tctcggactg gagatttgtc ctgtctggat | 900 |
| cttacagctt cacctggctc tgcggacacg tgcaccggaa catcctctcc aagttcacag | 960 |
| gccaggcggt ggagctgttt gacgaggagt tccgccacct ctacgcctcc tccaagcctg | 1020 |
| tgatgggcct gaagtccccg cggctggtcg ccccgtccc gccggagca gccccggcca | 1080 |
| atggccgcct tagcagcagc agtggctccg ccagtgaccg cacgtcctcc aacccctca | 1140 |
| gcggccgctc ggcaggcagc caccccggta cccgaagtgt gtccgcgtct cagggccct | 1200 |
| gtagccccgc ggccccacac ccgcctccac cgccccggtt ccagccccac caaggcct | 1260 |
| ggggagcccc gagtcccag gcccacctct ccccgcggcc ccacgacggc ccgcccgccg | 1320 |
| ctgtctacag caacctgggg gcctacaggc ccacgcggct gcagctggag cagctgggcc | 1380 |
| tggtgccgag gctgactcca acctggaggc ccttcctgca ggcctcccct cacttctgaa | 1440 |
| ggtcccatcc cctgctgccc tccgcaggcc cagggctggg cactccctga cccaaaga | 1500 |
| cccacctcaa cgacgagtgg cgttgagcca cttccctttg aaaagacact caaaatcact | 1560 |
| gccatggttc aatgttccca ggccccaggc catccacttg ccggccccca ccagttcttg | 1620 |
| ggttccccgc tctagtttga cctgtgcagc acattccaga aggttccagg gaggttgtgg | 1680 |
| ggcagctaga ggacaaaatc atgaaaacag agtccctgtc ttccagagat catccggggc | 1740 |
| tttaatatta atggcccca aaactccgta agaagcagga aatgcagccc aagttttaca | 1800 |
| aatgggtaaa cagaggcact gagagataga tggtagtttg gtacttctgg ttcccagtgc | 1860 |
| ccaggaatgg tccactccca agaaattcag gaaagaaaga ctgaggagaa ggtgtgggaa | 1920 |
| cattctggat gtttcgggag agttgggaa actcctcctc ttaggaaagg ctaatactag | 1980 |
| ggtatccttg ggcccaatga attaggggtg aggccccaga acccgttatc tatgagttgt | 2040 |
| atggggagc catctgaagc tgtagccacc agggatgcag ctagctgagg agtttggggt | 2100 |
| gttgggttgg acaaggcagg ttagtagact cagattcttg cttcaaagag ccttgggctg | 2160 |
| gcctggaggt ccctggagtc tagactggac ctaggagctt gagttgtcag gggccaggac | 2220 |
| tggcccccact gcagtgccca ggccagtctt gagcagcagg gagggctcag ctgtccccag | 2280 |
| atccaggtgc ctctgaccag cctggtcacc tcctgaggaa taaatgctga acctcacaag | 2340 |
| ccccatcatt catttcttct caattcacag tgcccctctt tgtttctggg gtggaactag | 2400 |
| gtcctgaggg cacagcctag ctgagtgcaa agaaatatag gatgcttaga aagcatacag | 2460 |
| gaggggccag gcgtggtggc tcatgcctgt aatcccagaa ctttgggatg ccaaggtggt | 2520 |
| tggattacct gagatcaggt ggattacctg gtctcgagac cagcctgacc aatatggtga | 2580 |
| aaccccgtct ctactaaaaa tacaaaaatt aggctgagac aggagaattg cttgaaccca | 2640 |
| ggaagcagag gttgcaatga gctgagattg catcactgca ctccagcatg gcaacaaag | 2700 |
| caagactccg tcacagaaaa aaaaaaaaa aagagagaga gcatagagga gggttggcca | 2760 |
| gccctgtggt gggtgggatg tcagagacac ttcccagata agtaagagt taaccctgca | 2820 |
| cctcaggtgt gatagtgggg tcagtggtat gtgatccagg ctggggagcc agaggggagc | 2880 |
| aggtgccaac tccacatcct tctcctgttt ctaggccctc tcctcccttg tcggttttg | 2940 |
| gcggggaagc tcagccttcg ctgtggaggg acgagagcac agagctcttc ctcctggtgg | 3000 |
| cctctgaccc ctgacggcct gtggcatcct ccctagtccc ctctgcccat ccatccctct | 3060 |
| gttccaattc tccactgctc ccagcatgat ctggggcatc ttggcttctg gtttctttta | 3120 |

```
ttattattat tattattaat tattgtattc ctgtccttca cttttttcct ccttagttcc    3180
tgaaagtaaa caaaacaaaa caaaaacaaa aaaacaaaca acactttggt tcctgatggc    3240
tttctgaacc cagccctgac cttgttgttt cacagctgac ggctgagatg aggttagaat    3300
gactgggccc ggctgaacat tccaaattgg atttcaccat ctgctgagaa agtttaagga    3360
aggcaaagct tgccaggtca cagaagctcc caagcccagc tttccaaagg cctcagcctg    3420
tgcctgtgtc gagctcagtc ctgggagata ggggagaacc tgcaggcagg aacaagcccc    3480
cctactcctg accaccctcc atcagcagtc tcccctccgt ggtcgtcttt gttgacaaag    3540
gtgcagtttc tcctctcctg ggcacctgta acatgtgatg cgctgcctgc tgggaggtta    3600
ggtcggggct gccccggcga gtggagcatg agcagaaccg ccgagggtca cttctgggca    3660
gaagctttga gagcctgggt ccaggttgcc acatagaagc agctctccag ttgaaaccct    3720
cctctgccag cctggggtcc taagcgatga gcagaatccc ccactcccac cccaccaacc    3780
cacaatggat atgtagtgag caagaaataa acctttgttg tttaagcca               3829

<210> SEQ ID NO 32
<211> LENGTH: 585
<212> TYPE: DNA
<213> ORGANISM: Homo sapiens

<400> SEQUENCE: 32
gttcactggg cgtcttctgc ccggccccct cgcccacgtg aagaacgcca gggagctgtg      60
aggcagtgct gtgtggttcc tgccgtccgg actctttttc ctctactgag attcatctgt     120
gtgaaatatg agttggcgag gaagatcgac ctattattgg cctagaccaa ggcgctatgt     180
acagcctcct gaaatgattg ggcctatgcg gcccgagcag ttcagtgatg aagtggaacc     240
agcaacacct gaagaagggg aaccagcaac tcaatgtcag gatcctgcag ctgctcagga     300
gggagaggat gagggagcat ctgcaggtca agggccgaag cctgaagctc atagccagga     360
acagggtcac ccacagactg ggtgtgagtg tgaagatggt cctgatgggc aggagatgga     420
cccgccaaat ccagaggagg tgaaaacgcc tgaagaaggt gaaaagcaat cacagtgtta     480
aaagaagaca cgttgaaatg atgcaggctg ctcctatgtt ggaaatttgt tcattaaaat     540
tctcccaata aagctttaca gccttctgca aagaagtctt gcgca                    585

<210> SEQ ID NO 33
<211> LENGTH: 1780
<212> TYPE: DNA
<213> ORGANISM: Homo sapiens

<400> SEQUENCE: 33
gcagagctac catgtcctct tggagcagac agcgaccaaa aagcccaggg ggcattcaac      60
cccatgtttc tagaactctg ttcctgctgc tgctgttggc agcctcagcc tgggggggtca    120 ccctgagccc caaagactgc caggtgttcc gctcagacca tggcagctcc atctcctgtc    180
aaccacctgc cgaaatcccc ggctacctgc agccgacac cgtgcacctg gccgtggaat     240
tcttcaacct gacccacctg ccagccaacc tcctccaggg cgcctctaag ctccaagaat    300
tgcacctctc cagcaatggg ctggaaagcc tctcgcccga attcctgcgg ccagtgccgc    360
agctgagggt gctggatcta acccgaaacg ccctgaccgg gctgccccg ggcctcttcc     420 aggcctcagc caccctggac accctggtat tgaaagaaaa ccagctggag gtcctggagg    480
tctcgtggct acacggcctg aaagctctgg ggcatctgga cctgtctggg aaccgcctcc    540
```

```
ggaaactgcc ccccgggctg ctggccaact tcaccctcct gcgcacccTt gaccttgggg    600
agaaccagtt ggagaccttg ccacctgacc tcctgagggg tccgctgcaa ttagaacggc    660
tacatctaga aggcaacaaa ttgcaagtac tgggaaaaga tctcctcttg ccgcagccgg    720
acctgcgcta cctcttcctg aacggcaaca agctggccag ggtggcagcc ggtgccttcc    780
agggcctgcg gcagctggac atgctggacc tctccaataa ctcactggcc agcgtgcccg    840
aggggctctg ggcatcccta gggcagccaa actgggacat gcgggatggc ttcgacatct    900
ccggcaaccc ctggatctgt gaccagaacc tgagcgacct ctatcgttgg cttcaggccc    960
aaaaagacaa gatgttttcc cagaatgaca cgcgctgtgc tgggcctgaa gccgtgaagg   1020
gccagacgct cctggcagtg gccaagtccc agtgagacca ggggcttggg ttgagggtgg   1080
ggggtctggt agaacactgc aacccgctta acaaataatc ctgcctttgg ccgggtgcgg   1140
gggctcacgc ctgtaatccc agcactttgg gaggcccagg tgggcggatc acgaggtcag   1200
gagatcgaga ccatcttggc taacatggtg aaaccctgtc tctactaaaa atataaaaaa   1260
ttagccaggc gtggtggtgg gcacctgtag tcccagcaac tcgggaggct gaggcaggag   1320
aatggcgtga acttgggagg cggagcttgc ggtgagccaa gatcgtgcca ctgcactcta   1380
gcctgggcga cagagcaaga ctgtctcaaa aaaattaaaa ttaaaattaa aaacaaataa   1440
tcctgccttt tacaggtgaa actcggggct gtccatagcg gctgggaccc cgtttcatcc   1500
atccatgctt cctagaacac acgatgggct ttccttaccc atgcccaagg tgtgccctcc   1560
gtctggaatg ccgttccctg tttcccagat ctcttgaact ctgggttctc ccagcccctt   1620
gtccttcctt ccagctgagc cctggccaca ctggggctgc cttTctctga ctctgtcttc   1680
cccaagtcag ggggctctct gagtgcaggg tctgatgctg agtcccactt agcttggggt   1740
cagaaccaag gggtttaata aataacccctt gaaaactgga                        1780
```

<210> SEQ ID NO 34
<211> LENGTH: 1724
<212> TYPE: DNA
<213> ORGANISM: Homo sapiens

<400> SEQUENCE: 34

```
agagacaagc gagcttctgc gtctgactcg cagcttgaga ctggcggagg gaagcccgcc     60
caggctctat aaggagacaa ggttctgagc agacaggcca accggaggac aggattccct    120
ggaggccaca gaggagcacc aaggagaaga tctgcctgtg ggtccccatt gcccagcttt    180
tgcctgcact cttgcctgct gccctgacca gagtcatcat gtcttctgag cagaagagtc    240
agcactgcaa gcctgaggaa ggcgttgagg cccaagaaga ggccctgggc ctggtgggtg    300
cacaggctcc tactactgag gagcaggagg ctgctgtctc ctcctcctct cctctggtcc    360
ctggcaccct ggaggaagtg cctgctgctg agtcagcagg tcctcccag agtcctcagg    420
gagcctctgc cttacccact accatcagct tcacttgctg gaggcaaccc aatgagggtt    480
ccagcagcca agaagaggag gggccaagca cctcgcctga cgcagagtcc ttgttccgag    540
aagcactcag taacaaggtg gatgagttgg ctcatttTct gctccgcaag tatcgagcca    600
aggagctggt cacaaaggca gaaatgctgg agagagtcat caaaaattac aagcgctgct    660
ttcctgtgat cttcggcaaa gcctccgagt ccctgaagat gatctttggc attgacgtga    720
aggaagtgga ccccgccagc aacacctaca cccttgtcac ctgcctgggc ctttcctatg    780
atggcctgct gggtaataat cagatcttTc caagacagg ccttctgata atcgtcctgg    840
gcacaattgc aatggagggc gacagcgcct ctgaggagga aatctgggag gagctgggtg    900
```

```
tgatggggt gtatgatggg agggagcaca ctgtctatgg ggagcccagg aaactgctca      960
cccaagattg ggtgcaggaa aactacctgg agtaccggca ggtacccggc agtaatcctg     1020
cgcgctatga gttcctgtgg ggtccaaggg ctctggctga aaccagctat gtgaaagtcc     1080
tggagcatgt ggtcagggtc aatgcaagag ttcgcattgc ctacccatcc ctgcgtgaag     1140
cagctttgtt agaggaggaa gagggagtct gagcatgagt tgcagccagg ctgtgggga      1200
aggggcaggg ctgggccagt gcatctaaca gccctgtgca gcagcttccc ttgcctcgtg     1260
taacatgagg cccattcttc actctgtttg aagaaaatag tcagtgttct tagtagtggg     1320
tttctatttt gttggatgac ttggagattt atctctgttt ccttttacaa ttgttgaaat     1380
gttccttta  atggatggtt gaattaactt cagcatccaa gtttatgaat cgtagttaac     1440
gtatattgct gttaatatag tttaggagta agagtcttgt tttttattca gattgggaaa     1500
tccgttctat tttgtgaatt tgggacataa taacagcagt ggagtaagta tttagaagtg     1560
tgaattcacc gtgaaatagg tgagataaat taaaagatac ttaattcccg ccttatgcct     1620
cagtctattc tgtaaaattt aaaaaatata tatgcatacc tggatttcct tggcttcgtg     1680
aatgtaagag aaattaaatc tgaataaata attctttctg ttaa                      1724

<210> SEQ ID NO 35
<211> LENGTH: 3681
<212> TYPE: DNA
<213> ORGANISM: Homo sapiens

<400> SEQUENCE: 35
tgtaaatgct cttctgacta atgcaaacca tgtgtccata gaaccagaag atttttccag      60
gggaaaagag ccccacgcc ccgcccagct ataaggggcc atgcaccaag cagggtaccc      120
aggctgcaga ggtgccatgg ctgagtcaca cctgctgcag tggctgctgc tgctgctgcc     180
cacgctctgt ggcccaggca ctgctgcctg gaccacctca tccttggcct gtgcccaggg     240
ccctgagttc tggtgccaaa gctggagca agcattgcag tgcagagccc tagggcattg     300
cctacaggaa gtctggggac atgtgggagc cgatgaccta tgccaagagt gtgaggacat     360
cgtccacatc cttaacaaga tggccaagga ggccattttc caggacacga tgaggaagtt     420
cctggagcag gagtgcaacg tcctcccctt gaagctgctc atgccccagt gcaaccaagt     480
gcttgacgac tacttccccc tggtcatcga ctacttccag aaccagactg actcaaacgg     540
catctgtatg cacctgggcc tgtgcaaatc ccggcagcca gagccagagc aggagccagg     600
gatgtcagac cccctgccca aacctctgcg ggaccctctg ccagaccctc tgctggacaa     660
gctcgtcctc cctgtgctgc ccggggccct ccaggcgagg cctgggcctc acacacagga     720
tctctccgag cagcaattcc ccattcctct cccctattgc tggctctgca gggctctgat     780
caagcggatc caagccatga ttcccaaggg tgcgctagct gtggcagtgg cccaggtgtg     840
ccgcgtggta cctctggtgg cgggcggcat ctgccagtgc ctggctgagc gctactccgt     900
catcctgctc gacacgctgc tgggccgcat gctgcccag ctggtctgcc gcctcgtcct     960
ccggtgctcc atggatgaca gcgctggccc aaggtcgccg acaggagaat ggctgccgcg    1020
agactctgag tgccacctct gcatgtccgt gaccacccag gccgggaaca gcagcgagca    1080
ggccatacca caggcaatgc tccaggcctg tgttggctcc tggctggaca gggaaaagtg    1140
caagcaattt gtggagcagc acacgcccca gctgctgacc ctggtgccca gggggctggga    1200
tgcccacacc acctgccagg ccctcggggt gtgtgggacc atgtccagcc ctctccagtg    1260
```

```
tatccacagc cccgaccttt gatgagaact cagctgtcca gctgcaaagg aaaagccaag    1320
tgagacgggc tctgggacca tggtgaccag gctcttcccc tgctccctgg ccctcgccag    1380
ctgccaggct gaaaagaagc ctcagctccc acaccgccct cctcaccgcc cttcctcggc    1440
agtcacttcc actggtggac cacgggcccc cagccctgtg tcggccttgt ctgtctcagc    1500
tcaaccacag tctgacacca gagcccactt ccatcctctc tggtgtgagg cacagcgagg    1560
gcagcatctg gaggagctct gcagcctcca cacctaccac gacctcccag ggctgggctc    1620
aggaaaaacc agccactgct ttacaggaca gggggttgaa gctgagcccc gcctcacacc    1680
cacccccatg cactcaaaga ttggatttta cagctacttg caattcaaaa ttcagaagaa    1740
taaaaaatgg gaacatacag aactctaaaa gatagacatc agaaattgtt aagttaagct    1800 tttttcaaaaa atcagcaatt ccccagcgta gtcaagggtg gacactgcac gctctggcat    1860
gatgggatgg cgaccgggca agcttcttc ctcgagatgc tctgctgctt gagagctatt    1920
gctttgttaa gatataaaaa gggtttctt tttgtctttc tgtaaggtgg acttccagct    1980
tttgattgaa agtcctaggg tgattctatt tctgctgtga tttatctgct gaaagctcag    2040
ctggggttgt gcaagctagg gacccattcc tgtgtaatac aatgtctgca ccaatgctaa    2100
taaagtccta ttctctttta tgagaaagaa aaagacaccg tcctttaaag tgctgcagta    2160
tggccagacg tggtggctca cacctgcaat cccagcacct taggaggccg aggcaggagg    2220
atccttgagg tcaggagttc gagaccagcc tcgccaacat ggtgaaaccc catttctact    2280
aaaaatacaa aaaattagcc aagtgtggtg gcatatgcct gtaatcccaa ctactcagaa    2340
ggccgaggca ggagaattac ttgaacgcag gagaatcact gcagcccagg aggcagaggt    2400
tgcagtgagc cgagattgca ccactgcact ccagcctggg tgacagagca agactccatc    2460
tcagtaaata aataaataaa taaaaagcgc tgcagtagct gtggcctcac cctgaagtca    2520
gcgggcccag gcctacctca ctctctccct tggcagagaa gcagacgtcc atagctcctc    2580
tccctcacaa gcgctcccag cctgccctcc agctgctgct ctcccctccc agtctctact    2640
cactgggatg aggttaggtc atgaggacac caaaaaccta aaaataaaca aaaagccaaa    2700
caagccttag cttttcttaa agactgaaat gcctggaagt gtccctttat ttataaaata    2760
acttttgtca tatttcttat acatgtttct tgtaagaaat tcagaaacta cagacaaaga    2820
gagtggaaat tacccactgt caggcctctg agcccaagct aagccatcat atcccctgtg    2880
ccctgcacgt atacacccag atggcctgaa gcaactgaag atccacaaaa gaagtgaaaa    2940
tagccagttc ctgccttaac tgatgacatt ccaccattgt gatttgttcc tgccccaccc    3000
taactgatca attgaccttg tgacaataca ccttccccac ccttgagaag gtgctttgta    3060
atattctccc cacccaccc acgcccgcac ccccgcaccc ttaagaaggt attttgtaat    3120
attctctccg ccattgagaa tgtgctttgt aagatccacc ccctgcccac aaaaaattgc    3180
tcctaactcc accgcctatc ccaaacctac aagaactaat gataatccca ccacccttg    3240 ctgactcttt ttggactcag cccacctgca cccaggtgat taaaaagctt tattgttcac    3300
acaaagcctg tttggtagtc tcttcacagg gaagcatgtg acacccacaa tcccacctag    3360
cccaggagag agctacggca gggtgtgtgt tttgacactg agcttggggc ttttttccatc    3420 ttctccccac agcctctggc tccacacctc caccgttcaa gcgccagaaa gagctgtcta    3480
tgcagcctgc tcttgggcct ggggatgaga cacacaattc attggctcct ggattttaag    3540
tagacatttg taaatctata gctaactact gtccttaaag ccattgtttc cattacaaaa    3600
tccaactctc tgagagaaaa gggtgtttta aatttaaaaa aataaaaaca aaaagtttg    3660
```

```
attgagaaaa aaaaaaaaaa a                                              3681

<210> SEQ ID NO 36
<211> LENGTH: 481
<212> TYPE: DNA
<213> ORGANISM: Homo sapiens

<400> SEQUENCE: 36
gggaacgcgg cggagctgtg agccggcgac tcgggtccct gaggtctgga ttctttctcc     60
gctactgaga cacggcggac acacacaaac acagaaccac acagccagtc ccaggagccc    120
agtaatggag agccccaaaa agaagaacca gcagctgaaa gtcgggatcc tacacctggg    180
cagcagacag aagaagatca ggatacagct gagatcccag gtgctgggaa gggaaatgcg    240
cgacatggaa ggtgatctgc aagagctgca tcagtcaaac accggggata aatctggatt    300
tgggttccgg cgtcaaggtg aagataatac ctaaagagga acactgtaaa atgccagaag    360
caggtgaaga gcaaccacaa gtttaaatga agacaagctg aaacaacgca agctggtttt    420
atattagata tttgacttaa actatctcaa taaagttttg cagctttcac caaaaaaaaa    480
a                                                                    481
```

DETECTION OF LUNG NEOPLASIA BY AMPLIFICATION OF RNA SEQUENCES

CROSS REFERENCE TO RELATED APPLICATIONS

The present invention is a continuation of U.S. patent application Ser. No. 15/587,806, filed May 5, 2017, which claims priority benefit of U.S. Provisional Patent Application No. 62/332,419, filed May 5, 2016, each of which is incorporated by reference in its entirety.

SEQUENCE LISTING

The text of the computer readable sequence listing filed herewith, titled "34787-303_SEQUENCE-_LISTING_ST25", created 10/23/2020, having a file size of 35,735 bytes, is hereby incorporated by reference in its entirety.

FIELD OF THE INVENTION

Provided herein is technology relating to detecting neoplasia and particularly, but not exclusively, to methods, compositions, and related uses for detecting neoplasms such as lung cancer.

BACKGROUND OF THE INVENTION

Lung cancer is the most frequent cause of death among men and women younger than 85 years in the US. It accounts for 27% of all cancer deaths and 221,000 lost lives annually. This mortality rate exceeds that of the next 4 highest ranking cancers combined. Gene expression profiling has confirmed unique mRNA expression in cancers and can be used as an approach for detection of lung malignancies. An mRNA multi-marker approach to detect all subtypes of lung cancer needs to be explored. This study assesses the value of measuring expression levels of multiple mRNA markers in detecting lung cancer of different subtypes.

SUMMARY OF THE INVENTION

This technology is in the field of nucleic acid detection and quantification. Specifically, the technology addresses the detection and quantification of RNA in samples using single-tube RT-PCR-Invasive cleavage reaction (RT-QuARTS).

In some embodiments the technology provides methods of screening for a lung neoplasm in a sample obtained from a subject, the methods comprising, e.g., a) assaying a sample from a subject for an amount of at least one RNA marker selected from the group consisting of GAGE12D, FAM83A, LRG1, XAGE-1 d, MAGEA4, SFTPB, AKAP4, and CYP24A1; b) assaying the sample for an amount of a reference marker in the sample; c) comparing the amount of the at least one RNA marker to the amount of the reference marker to determine a level of expression for the at least one marker gene in the sample; and d) generating a record reporting the expression for the at least one marker gene in said sample. In some embodiments the method comprises obtaining a sample comprising RNA from a subject and treating the RNA with a reverse transcriptase, preferably MMLV reverse transcriptase, to form a cDNA copy of at least a portion of the RNA. In preferred embodiments, the cDNA is created and detected in a single vessel, without opening the vessel, e.g., to add additional reagents.

In some embodiments the at least one RNA marker is at least two markers. In some preferred embodiments the at least one RNA marker comprises the group consisting of GAGE, FAM83A, LRG1 and MAGEA4 markers, while in some embodiments, the at least one RNA marker comprises the group consisting of GAGE, FAM83A, LRG1, CYP24A1, XAGE1D and MAGEA4 markers. In some embodiments, the reference marker is an RNA, preferably an RNA selected from the group consisting of CASC3 mRNA, β-actin mRNA, U1 snRNA and U6 snRNA.

In some embodiments the technology comprises assaying RNA using one or more of a polymerase chain reaction, nucleic acid sequencing, mass spectrometry, mass-based separation, or target capture. In particularly preferred embodiments, the assaying comprises using a flap endonuclease assay, such as a QuARTS assay, as described hereinbelow.

In some embodiments, assaying the expression of the RNA marker comprises detecting increased or decreased expression of the RNA marker relative to a normal expression of the marker.

Samples suitable for analysis using the technology are not limited to a particular sample type. In some embodiments the sample is a tissue sample, a blood sample, a serum sample, or a sputum sample. In certain preferred embodiments the tissue sample comprises lung tissue.

The technology further provides kits, e.g., for practicing the technology. For example, in some embodiments the technology provides a kit comprising:

a) at least one oligonucleotide, wherein at least a portion of said oligonucleotide specifically hybridizes to a marker RNA selected from the group consisting of GAGE12D, FAM83A, LRG1, XAGE-1 d, MAGEA4, SFTPB, AKAP4, and CYP24A1, and b) at least one additional oligonucleotide, wherein at least a portion of said additional oligonucleotide specifically hybridizes to a reference nucleic acid.

In preferred embodiments the kit comprises at least two additional oligonucleotides. In some embodiments, the kit further comprises one or more components selected from the group consisting of reverse transcriptase, flap endonuclease, DNA polymerase, and a FRET cassette.

In some embodiments the at least one RNA marker is selected from the group consisting of GAGE, FAM83A, LRG1, CYP24A1, XAGE1D and MAGEA4, and in some embodiments the RNA marker is selected from the group consisting of GAGE, FAM83A, LRG1 and MAGEA4. In certain preferred embodiments the kit comprises at least 4 oligonucleotides, wherein each of the markers in the group consisting of GAGE, FAM83A, LRG1, and MAGEA4 specifically hybridizes to at least one of said 4 oligonucleotides. In other embodiments, the kit comprises at least 6 oligonucleotides, wherein each of the markers in the group consisting of GAGE, FAM83A, LRG1, CYP24A1, XAGE1D and MAGEA4 specifically hybridizes to at least one of said 6 oligonucleotides. In preferred embodiments at least one oligonucleotide is selected from one or more of a capture oligonucleotide, a pair of nucleic acid primers, a nucleic acid probe, and an invasive oligonucleotide.

The technology is not limited to which particular reference marker RNA is used, and many are known in the field. In preferred embodiments, the reference marker is an RNA selected from the group consisting of CASC3, β-actin, U1 and U6 RNA The technology further comprises compositions such as mixtures, e.g., reaction mixtures. In some embodiments the technology provides a mixture comprising a complex of at least one RNA marker selected from the group consisting of GAGE12D, FAM83A, LRG1, XAGE-1 d, MAGEA4, SFTPB, AKAP4, and CYP24A1 and an oligonucleotide that specifically hybridizes to the RNA marker. In preferred embodiments, the composition further comprises a complex of at least one reference marker and an oligonucleotide that specifically hybridizes to the reference RNA marker. In some embodiments the at least one RNA marker is selected from the group consisting of GAGE, FAM83A, LRG1, CYP24A1, XAGE1D and MAGEA4, while in some embodiments the least one RNA marker is selected from the group consisting of GAGE, FAM83A, LRG1 and MAGEA4. In preferred embodiments the composition comprises a reference marker that is an RNA selected from the group consisting of CASC3, β-actin, U1 RNA and U6 RNA. In particularly preferred embodiments, the oligonucleotide is selected from one or more of a capture oligonucleotide, a pair of nucleic acid primers, a nucleic acid probe, and an invasive oligonucleotide. Preferably the composition comprises a nucleic acid probe oligonucleotide comprising a reporter molecule, e.g., a fluorophore, and/or a flap sequence.

In some embodiments, the composition further comprises one or more components selected from the group consisting of reverse transcriptase, (e.g., MMLV reverse transcriptase), flap endonuclease, thermostable DNA polymerase, and a FRET cassette. In preferred embodiments, the DNA polymerase is a bacterial DNA polymerase.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the "sensitivity" of a given marker (or set of markers used together) refers to the percentage of samples that report a marker value (e.g., an expression marker) above a threshold value that distinguishes between neoplastic and non-neoplastic samples. In some embodiments, a positive is defined as a histology-confirmed neoplasia that reports a marker value above a threshold value (e.g., the range associated with disease), and a false negative is defined as a histology-confirmed neoplasia that reports a marker value below the threshold value (e.g., the range associated with no disease). The value of sensitivity, therefore, reflects the probability that a measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a marker value (e.g., an expression marker) below a threshold value that distinguishes between neoplastic and non-neoplastic samples. In some embodiments, a negative is defined as a histology-confirmed non-neoplastic sample that reports a marker value below the threshold value (e.g., the range associated with no disease) and a false positive is defined as a histology-confirmed non-neoplastic sample that reports a marker value above the threshold value (e.g., the range associated with disease). The value of specificity, therefore, reflects the probability that a marker measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target nucleic acid is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

The term "marker", as used herein, refers to a substance (e.g., a nucleic acid, or a region of a nucleic acid, or a protein) that may be used to distinguish non-normal cells (e.g., cancer cells) from normal cells, e.g., based on presence, absence, or status (e.g., post-transcriptional processing) of the marker substance.

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids (DNA, RNA, miRNA, etc.), polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the expression of a marker described herein.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816, WO 2006/050499; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110, 684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210, 884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110, 677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in U.S. Pat. Nos. 8,361,720; 8,715,937; 8,916,344; and 9,212,392, incorporated herein by reference in their entireties for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above. The term "flap oligonucleotide" refers to an oligonucleotide cleavable in a detection assay, such as an invasive cleavage assay, by a flap endonuclease. In preferred embodiments, a flap oligonucleotide forms an invasive cleavage structure with other nucleic acids, e.g., a target nucleic acid and an invasive oligonucleotide.

As used herein, the term "PCR-invasive cleavage assay" refers to an assay in which target nucleic acid is amplified and amplified nucleic acid is detected simultaneously using a signal-amplifying invasive cleavage assay employing a FRET cassette, and in which the assay reagents comprise a mixture containing DNA polymerase, FEN-1 endonuclease, a primary probe comprising a portion complementary to a target nucleic acid, and a hairpin FRET cassette. PCR-invasive cleavage assays include the QuARTS assays described in U.S. Pat. Nos. 8,361,720; 8,715,937; 8,916, 344; and 9,212,392, and the amplification assays of U.S. Pat. No. 9,096,893, as diagrammed in FIG. 1 of that patent, each of which is incorporated herein by reference for all purposes.

As used herein, the term "PCR-invasive cleavage assay reagents" refers to one or more reagents for detecting target sequences in a PCR-invasive cleavage assay, the reagents comprising nucleic acid molecules capable of participating in amplification of a target nucleic acid and in formation of an invasive cleavage structure in the presence of the target sequence, in a mixture containing DNA polymerase, FEN-1 endonuclease and a FRET cassette, and optionally a reverse transcriptase.

As used herein, the term "FRET cassette" refers to a hairpin oligonucleotide that contains a fluorophore moiety and a nearby quencher moiety that quenches the fluorophore. Hybridization of a cleaved flap (e.g., from cleavage of a target-specific probe in a PCR-invasive cleavage assay) with a FRET cassette produces a secondary substrate for the flap endonuclease, e.g., a FEN-1 enzyme. Once this substrate is formed, the 5' fluorophore-containing base is cleaved from the cassette, thereby generating a fluorescence signal. In preferred embodiments, a FRET cassette comprises an unpaired 3' portion to which a cleavage product, e.g., a portion of a cleaved flap oligonucleotide, can hybridize to from an invasive cleavage structure cleavable by a FEN-1 endonuclease.

A nucleic acid "hairpin" as used herein refers to a region of a single-stranded nucleic acid that contains a duplex (i.e., base-paired) stem and a loop, formed when the nucleic acid comprises two portions that are sufficiently complementary to each other to form a plurality of consecutive base pairs.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor flurophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FEN-1" in reference to an enzyme refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "FEN-1 activity" refers to any enzymatic activity of a FEN-1 enzyme, including but not limited to flap endonuclease (FEN), nick exonuclease (EXO), and gap endonuclease (GEN) activities (see, e.g., Shen, et al., BioEssays Volume 27, Issue 7, Pages 717-729, incorporated herein by reference).

As used herein, the term "primer annealing" refers to conditions that permit oligonucleotide primers to hybridize to template nucleic acid strands. Conditions for primer annealing vary with the length and sequence of the primer and are generally based upon the $T_m$ that is determined or calculated for the primer. For example, an annealing step in an amplification method that involves thermocycling involves reducing the temperature after a heat denaturation step to a temperature based on the $T_m$ of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

A sample "suspected of containing" a nucleic acid may contain or not contain the target nucleic acid molecule.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the terms "reverse transcription" and "reverse transcribe" refer to the use of a template-dependent polymerase to produce a DNA strand complementary to an RNA template. A polymerase capable of producing a DNA strand complementary to an RNA template is generally referred to as a "reverse transcriptase" or as a polymerase that has "reverse transcriptase activity".

As used herein, the term "abundance of nucleic acid" refers to the amount of a particular target nucleic acid sequence present in a sample or aliquot. The amount is generally referred to in terms of mass (e.g., µg), mass per unit of volume (e.g., µg/µl); copy number (e.g., 1000 copies, 1 attomole), or copy number per unit of volume (e.g., 1000 copies per ml, 1 attomole per µl). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions at prior to incubation or, in the case of PCR, in the initial cycles, in which there is little change in signal.

The term "no template control" and "no target control" (or "NTC") as used herein in reference to a control reaction refers to a reaction or sample that does not contain template or target nucleic acid. It is used to verify amplification quality.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein in reference to real-time detection during an amplification reaction that is thermal cycled refers to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the amount of RNA marker(s) or reference markers in an assay or sample.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides.

The term "system" as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DESCRIPTION OF THE DRAWINGS

FIG. 2 compares the effects of different amounts of reverse transcriptase and different reverse transcription conditions on the detection of known amounts of target RNA in RT-QuARTS assays.

FIG. 3 shows graphs showing standard curves measuring marker LRG1 RNA. Panel A describes the dilution series, the average Cp value at each dilution, and the calculated strands/reaction calculated from the amplification plots shown in panel B. Panel C shows a graph comparing the Cp compared to the log of the amount of RNA present in the sample.

FIG. 5 shows graphs comparing the sensitivity and specificity when samples are analyzed using the combinations of four or six expression markers, as listed above each panel.

DETAILED DESCRIPTION OF THE INVENTION

Figure 1:
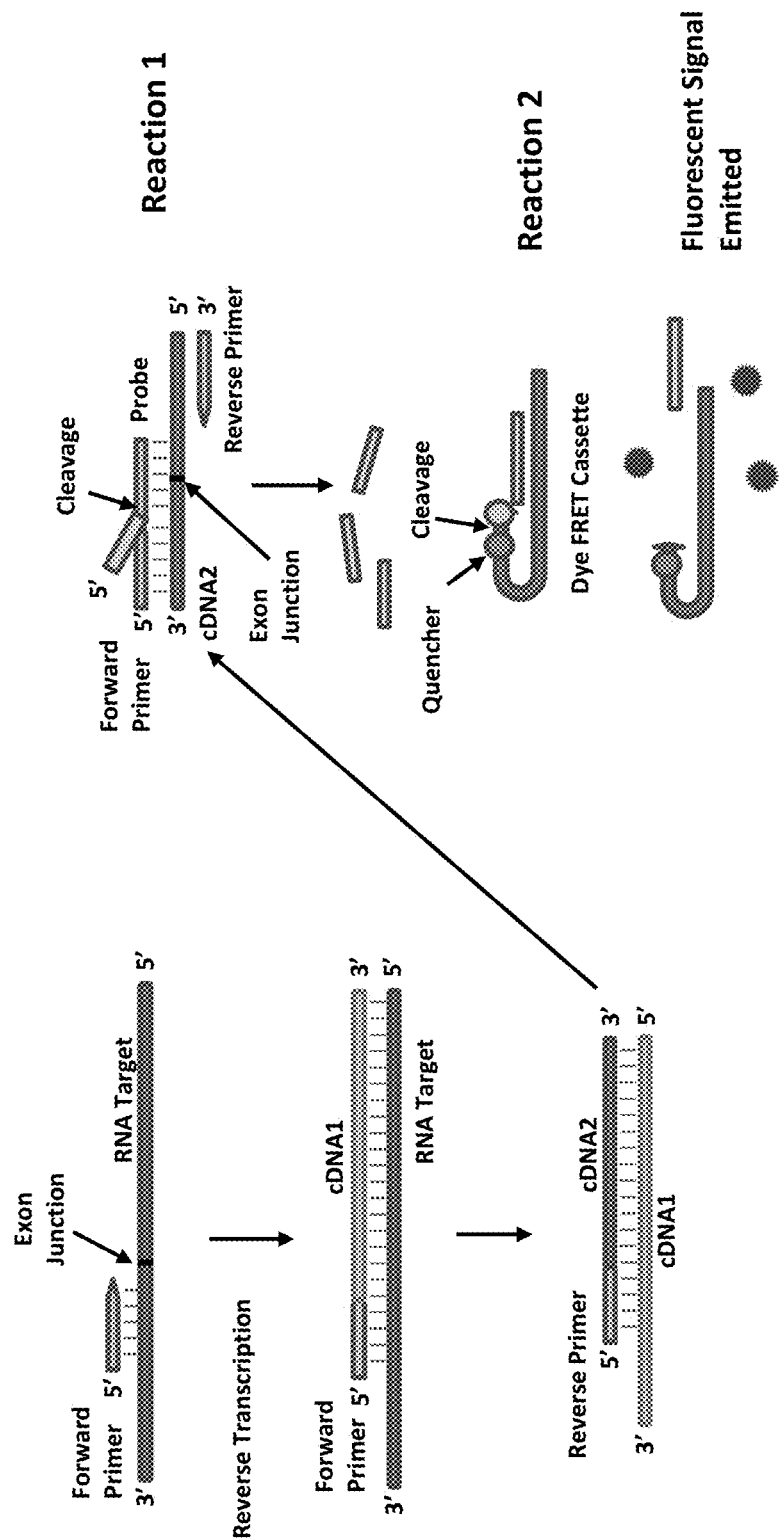
FIG. 1 shows a schematic diagram of a combined reverse transcription-QuARTS flap endonuclease detection assay for real-time detection of RNA. Use of multiple different probe flap/FRET cassette dye combinations allows multiple different target nucleic acids to be detected together in multiplex reactions.

Provided herein is technology relating to RNA expression markers for use in assays for detection and quantification of RNA. In particular, the technology relates to use of RNA-based gene expression assays to detect lung cancer.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

The methods and compositions provided herein relate to characterizing the expression from marker genes by characterizing RNA molecules ("RNA markers") in a sample, wherein the RNA presence, absence, or status (e.g., with respect to post-transcription modifications or processing) is indicative of neoplasia. Accordingly, provided here are compositions and method directed toward analysis of RNA markers that correlate with lung neoplasia. In preferred embodiments the technology provides assays wherein RNA markers are reverse transcribed, amplified, and detected in real time in a single reaction mixture, and in a single vessel.

Also provided herein are compositions and kits for practicing the methods. For example, in some embodiments, reagents (e.g., primers, probes) specific for one or more RNA expression markers are provided alone or in sets (e.g., sets of primers pairs for amplifying a plurality of RNA markers). Additional reagents for conducting a detection assay may also be provided (e.g., enzymes, buffers, positive and negative controls for conducting QuARTS assays, RT-QuARTS assays, PCR, sequencing, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

The technology relates to the analysis of any sample associated with lung cancer. For example, in some embodiments the sample comprises a tissue and/or biological fluid obtained from a patient. In some embodiments, the sample comprises a secretion. In some embodiments, the sample comprises sputum, blood, serum, plasma, lung tissue samples, or lung cells. In some embodiments, the subject is human. Such samples can be obtained by any number of means known in the art, such as will be apparent to the skilled person.

I. RNA Detection Assays to Detect Lung Cancer

Eight candidate mRNA markers (GAGE12D, FAM83A, LRG1, XAGE-1 d, MAGEA4, SFTPB, AKAP4, and CYP24A1) were selected based on discrimination reported in the literature. As described below, samples from 246 patients (119 controls, 127 lung cancer cases) were tested. The lung cancer cases comprised adena (65), squamous (34), large cell (13), small cell (4) and others carcinomas (11). The controls were from patients having benign lung nodules (37), normal lung (60), chronic obstructive pulmonary disorder (COPD) (10), and normal lung adjacent to tumor (12). Cases and controls included smokers and non-smokers.

Messenger RNA expression levels were assayed in a single-tube reverse transcription QuARTS (Quantitative Allele-Specific Real-time Target and Signal amplification) as described herein below, a reaction configuration that simultaneously measures copy numbers of two mRNA markers and a housekeeping reference mRNA (CASC3). To account for sample-to-sample variability, relative gene expression values of each mRNA marker were calculated by dividing the copy numbers obtained for each of the mRNAs by the CASC3 mRNA copy number.

Receiver operator characteristic (ROC) curve analyses resulted in an area under the curve (AUC) of 0.976. At 100% specificity, the mRNA panel of 6 markers achieved a sensitivity of 92.1% for all cancers (117/127) and 93.9% for adenocarcinoma and squamous carcinoma combined (93/99).

II. RNA Detection Assays and Kits

The markers described herein find use in a variety of RNA expression assays, e.g., qRT-PCR, digital PCR, gene expression arrays, etc. In some embodiments, a modified version of a quantitative real-time target and signal amplification (QuARTS) assay is used to evaluate gene expression. In DNA detection, three reactions occur during each QuARTS assay, including amplification (reaction 1) and target probe cleavage (reaction 2) in the primary reaction; and FRET cleavage and fluorescent signal generation (reaction 3) in the secondary reaction. After the first few cycles generate initial amounts of cleaved probe, these reactions occur essentially concurrently. As modified herein, a reverse transcription step is included to produce cDNA for QuARTS flap assay detection.

When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. A QuARTS flap endonuclease assay can detect multiple targets in a single reaction vessel, e.g., by using FRET cassettes with different dyes.

Methods of isolating RNA from samples are known in the art. For example, RNA isolation methods may comprise one or more of organic extraction, ultrafiltration, hybrid capture, etc. In some embodiments, cells or lysed samples containing RNA may be added directly to assay reactions without purification.

In some embodiments, the sample comprises blood, serum, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a RNA is isolated from blood or from a plasma sample using a hybrid capture method, e.g., using target-specific binding materials (e.g., oligonucleotides) on solid supports.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker expression over time. Changes in expression, as well as the absence of change in expression, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Applications

In some embodiments, diagnostic assays identify the presence of a disease or condition in an individual. In some embodiments, the disease is cancer (e.g., lung cancer). In preferred embodiments, markers whose aberrant expression is associated with a lung cancer (e.g., one or more markers selected GAGE12D, FAM83A, LRG1, XAGE-1 d, MAGEA4, SFTPB, AKAP4, and CYP24A1) are used. In some embodiments, an assay further comprises detection of a reference nucleic acid (e.g., CASC3 or β-actin mRNAs; U1 and U6 snRNAs, etc.).

In some embodiments, the technology finds application in treating a patient (e.g., a patient with lung cancer, with early stage lung cancer, or who may develop lung cancer), the method comprising determining the expression levels of one or more markers as provided herein and administering a treatment to the patient based on the results of determining the expression levels. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments, the technology finds application in methods for diagnosing lung cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker, the expression of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., analyzing expression) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers disclosed herein.

Further, in some embodiments of the technology, multiple determinations of the biomarkers over time can be made to facilitate diagnosis and/or prognosis. A temporal change in the biomarker can be used to predict a clinical outcome, monitor the progression of lung cancer, and/or monitor the efficacy of appropriate therapies directed against the cancer. In such an embodiment for example, one might expect to see a change in the expression of one or more biomarkers disclosed herein (and potentially one or more additional biomarker(s), if monitored) in a biological sample over time during the course of an effective therapy.

The technology further finds application in methods for determining whether to initiate or continue prophylaxis or treatment of a cancer in a subject. In some embodiments, the method comprises providing a series of biological samples over a time period from the subject; analyzing the series of biological samples to determine expression of at least one biomarker disclosed herein in each of the biological samples; and comparing any measurable change in the expression of one or more of the biomarkers in each of the biological samples. Any changes in the expression of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Expression can be measured in each of the samples taken from different time points and qualitative and/or quantitative differences noted. A change in the expression of the biomarkers from the different samples can be correlated with risk for developing lung, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted above, in some embodiments multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the expression of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome (e.g., suffering from lung cancer) may be very low.

In some embodiments, a statistical analysis associates a prognostic indicator with a predisposition to an adverse outcome. For example, in some embodiments, an expression level different from that in a normal control sample obtained from a patient who does not have a cancer can signal that a subject is more likely to suffer from a cancer than subjects with a level that is more similar to the expression level in the control sample, as determined by a level of statistical significance. Additionally, a change in expression level from a baseline (e.g., "normal") level can be reflective of subject prognosis, and the degree of change in expression can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in expression of a prognostic or diagnostic biomarker disclosed herein can be established, and the degree of change in the expression of the biomarker in a biological sample is simply compared to the threshold degree of change in the expression. A preferred threshold change in the expression level for biomarkers provided herein is about 5%, about 10%, about 15%, about 20%, about 25%, about 30%, about 50%, about 75%, about 100%, and about 150%. In yet other embodiments, a "nomogram" can be established, by which expression of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present expression levels of a biomarker as a function of assay units, e.g., fluorescent signal intensity, if a fluorescent label is used. Using samples taken from multiple donors, standard curves can be provided for control expression of the one or more biomarkers in normal tissue, as well as for "at-risk" levels of the one or more biomarkers in tissue taken from donors with lung cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker expression over time. Changes in expression, as well as the absence of change in expression, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having lung cancer if, when compared to a control expression, there is a measurable difference in the expression of at least one biomarker in the sample. Conversely, when no change in expression is identified in the biological sample, the subject can be identified as not having lung cancer, not being at risk for the cancer, or as having a low risk of the cancer. In this regard, subjects having lung cancer or risk thereof can be differentiated from subjects having low to substantially no cancer or risk thereof. Those subjects having a risk of developing lung cancer can be placed on a more intensive and/or regular screening schedule. On the other hand, those subjects having low to substantially no risk may avoid being subjected to screening procedures, until such time as a future screening, for example, a screening conducted in accordance with the present technology, indicates that a risk of lung cancer has appeared in those subjects.

As mentioned above, depending on the embodiment of the method of the present technology, detecting a change in expression of the one or more biomarkers can be a qualitative determination or it can be a quantitative determination. As such, the step of diagnosing a subject as having, or at risk of developing, lung cancer indicates that certain threshold measurements are made, e.g., the expression of the one or more biomarkers in the biological sample varies from a predetermined control expression. In some embodiments of the method, the control expression is any detectable expression of the biomarker. In other embodiments of the method where a control sample is tested concurrently with the biological sample, the predetermined expression is the expression in the control sample. In other embodiments of the method, the predetermined expression is based upon and/or identified by a standard curve. In other embodiments of the method, the predetermined expression is a specifically state or range of state. As such, the predetermined expression can be chosen, within acceptable limits that will be apparent to those skilled in the art, based in part on the embodiment of the method being practiced and the desired specificity, etc.

Over recent years, it has become apparent that circulating epithelial cells, representing metastatic tumor cells, can be detected in the blood of many patients with cancer. Molecular profiling of rare cells is important in biological and clinical studies. Applications range from characterization of circulating epithelial cells (CEpCs) in the peripheral blood of cancer patients for disease prognosis and personalized treatment (See e.g., Cristofanilli M, et al. (2004) N Engl J Med 351:781-791; Hayes D F, et al. (2006) Clin Cancer Res 12:4218-4224; Budd G T, et al., (2006) Clin Cancer Res 12:6403-6409; Moreno J G, et al. (2005) Urology 65:713-718; Pantel et al., (2008) Nat Rev 8:329-340; and Cohen S J, et al. (2008) J Clin Oncol 26:3213-3221). Accordingly, embodiments of the present disclosure provide compositions and methods for detecting the presence of metastatic cancer in a subject by identifying the presence of expression markers in plasma or whole blood.

EXPERIMENTAL EXAMPLES

Tissue Extraction.

Tissue samples were obtained from various commercial and non-commercial sources (Asuragen, BioServe, ConversantBio, Cureline, Mayo Clinic, M D Anderson, and PrecisionMed). Tissue sections were examined by a pathologist, who circled histologically distinct lesions to direct careful micro-dissection. Total nucleic acid extraction was performed using the Promega Maxwell RSC system. FFPE slides were scraped and extracted using the Maxwell® RSC DNA FFPE Kit (#AS1450) using the manufacturer's procedure but skipping the RNase digestion step. The same procedure was used for FFPE bulk curls. For frozen punch biopsy samples, a modified procedure using the lysis buffer from the RSC DNA FFPE kit with the Maxwell® RSC Blood DNA kit (#AS1400) was utilized omitting the RNase step. Prior to testing, samples were diluted 1:5 in 20 ng/µL tRNA in 10 mM TrisHCl, pH 8.0, 0.1 mM EDTA.

Gene Expression Markers

Gene expression markers tested comprised AKAP4GAGE12D, FAM83A, SFTPB (Pro-Surfactant B), XAGE-1D, CYP24A1, LRG1, and MAGEA4, and one reference gene expression were tested on lung cancer tissue samples. Expression of CASC3 was used as a reference marker.

Lung Tissue Samples 127 cancer tissue samples and 119 normal lung tissue samples were tested. The tissue types tested are summarized in the following tables:

| Cancer Tissue Subtypes | N |
|---|---|
| Adenocarcinoma | 65 |
| Bronchioloalveolar | 6 |
| Large cell carcinoma | 13 |

-continued

| | |
|---|---|
| Neuroendocrine | 2 |
| Small cell carcinoma | 4 |
| Squamous cell carcinoma | 34 |
| Unknown | 3 |

| Normal Tissue | N |
|---|---|
| Benign lung nodules | 37 |
| Adjacent normal tissue | 72 |
| COPD tissue | 10 |

RT-QuARTS.

A QuARTS flap endonuclease assay reaction was modified to add a reverse transcription step. The assay probes were designed to span exon junctions so that the RT-QuARTS assay would specifically detect mRNA targets rather than the corresponding genomic loci. Briefly, the technique combines a reverse transcription step to convert the RNA target into a cDNA strand, a polymerase based target amplification and a simultaneous invasive cleavage signal amplification reaction (FIG. 1). The format results in a real-time accumulation of fluorescent signal in proportion to the amount of target mRNA. It produces a similar output to quantitative RT-PCR, but with the added sensitivity and specificity resulting from the addition of the invasive cleavage reaction. RT-QuARTS reactions comprising different amounts of Molony Murine Leukemia Virus (MMLV) reverse transcriptase and different dilutions of RNA were conducted using a reverse transcription reactions for 10 to 45 minutes. FIG. 2 provides a table comparing the results of the different reaction conditions.

Each triplex RT-QuARTS assay as describe below consists of one mRNA target reporting to FAM, one to HEX, and the reference mRNA to Quasar 670. Standard curves for each assay were generated by serially diluting known quantities of in vitro-produced transcripts for each marker. Standard curves were created by plotting Cp value by Log input strands. The resulting slope and intercept values were used to convert the Cp values of the unknown samples to mRNA strand values. Oligonucleotide sequences for the assays are shown in Table 1.

In vitro transcripts for each target were made from templates containing the DNA sequence amplified in the QuARTS reaction with additional flanking 5' and 3' sequences coupled to a T7 promoter. In vitro transcription was done using the T7 Ribomax system (Promega) and the resulting transcripts were quantitated with the Quant-iT RNA assay kit (Thermo Fisher Scientific).

Without reverse transcription, an exemplary QuARTS reaction typically comprises approximately 400-600 nmol/l (e.g., 500 nmol/l) of each primer and detection probe, approximately 100 nmol/l of the invasive oligonucleotide, approximately 600-700 nmol/l of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/µl FEN-1 endonuclease (e.g., Cleavase® 2.0, Hologic, Inc.), 1 unit Taq DNA polymerase in a 30 µl reaction volume (e.g., GoTaq® DNA polymerase, Promega Corp., Madison, Wis.), 10 mmol/l 3-(n-morpholino) propanesulfonic acid (MOPS), 7.5 mmol/l $MgCl_2$, and 250 µmol/l of each dNTP. Exemplary QuARTS cycling conditions are as shown in the table below. In some applications, analysis of the quantification cycle ($C_q$) provides a measure of the initial number of target DNA strands (e.g., copy number) in the sample.

RT-QuARTS reactions contained 20U of MMLV reverse transcriptase (MMLV-RT), 219 ng of Cleavase® 2.0, 1.5U of GoTaq® DNA Polymerase, 200 nM of each primer, 500 nM each of probe and FRET oligonucleotides, 10 mM MOPS buffer, pH7.5, 7.5 mM $MgCl_2$, and 250 µM each dNTP. Reactions were run on a Roche LightCycler 480 system under the following conditions: 42° C. for 30 minutes (RT reaction), 95° C. for 3 min, 10 cycles of 95° C. for 20 seconds, 63° C. for 30 sec, 70° C. for 30 sec, followed by 35 cycles of 95° C. for 20 sec, 53° C. for 1 min, 70° C. for 30 sec, and hold at 40° C. for 30 sec.

RT-QuARTS with Multiplex Preamplification

In some embodiments, RT-QuARTS assays may comprise a step of multiplex pre-amplification, e.g., to pre-amplify 10, 12, or more targets in as sample. Multiplex pre-amplification for QuARTS assays is described, e.g., in U.S. patent application Ser. Nos. 62/249,097, filed Oct. 30, 2015, and 62/332,295, filed May 5, 2016, each of which is incorporated herein by reference.

An RT-pre-amplification is conducted in a reaction mixture containing, e.g., 20U of MMLV reverse transcriptase, 1.5 U of GoTaq® DNA Polymerase, 10 mM MOPS buffer, pH7.5, 7.5 mM $MgCl_2$, 250 µM each dNTP, and oligonucleotide primers, (e.g., for 12 targets, 12 primer pairs/24 primers, in equimolar amounts (e.g., 200 nM each primer), or with individual primer concentrations adjusted to balance amplification efficiencies of the different targets). Thermal cycling times and temperatures are selected to be appropriate for the volume of the reaction and the amplification vessel. For example, the reactions may be cycled as follows:

| Stage | Temp/Time | #of Cycles |
|---|---|---|
| RT | 42° C./30' | 1 |
|  | 95° C./3' | 1 |
| Amplification 1 | 95° C./20" | 10 |
|  | 63° C./30" |  |
|  | 70° C./30" |  |
| Cooling | 4° C./Hold | 1 |

After thermal cycling, aliquots of the pre-amplification reaction (e.g., 10 µL) are diluted to 500 µL in 10 mM Tris, 0.1 mM EDTA, with or without fish DNA. Aliquots of the diluted pre-amplified DNA (e.g., 10 µL) are used in QuARTS PCR-flap assay, e.g., as described above.

In some embodiments, DNA targets, e.g., methylated DNA marker genes, genes corresponding to the RNA marker, etc., may be amplified and detected along with the reverse-transcribed cDNAs in a QuARTS assay reaction. In some embodiments, DNA and cDNA are co-amplified and detected in a single-tube reaction, i.e., without the need to open the reaction vessel at any point between combining the reagents and collecting the output data. In other embodiments, marker DNA from the same sample or from a different sample, may be separately isolated, with or without a bisulfite conversion step, and may be combined with sample RNA in an RT-QuARTS assay. In yet other embodiments, RNA and/or DNA samples may be pre-amplified as described above.

The amplification primers and probes used for reverse transcription, amplification, and the flap endonuclease reactions that occur in the RT-QuARTS assay as described herein are shown in Table 1, below:

TABLE 1

| Gene | Type | Sequence |
|---|---|---|
| AKAP4 | Forward Primer | 5'-GGACACTGAGAAGAAAGACCAGTC (SEQ ID NO: 1) |
|  | Reverse Primer | 5'-GGGAGCTTGTTTGAAAAGGCA (SEQ ID NO: 2) |
|  | Probe | 5'-CCACGGACGCTAAGACAGAGG/3C6/ (SEQ ID NO: 3) |
| CASC3 | Forward Primer | 5'-CTGCAACCACGGGAACTT (SEQ ID NO: 4) |
|  | Reverse Primer | 5'-GAGGTGGAGGTCCTGCTC (SEQ ID NO: 5) |
|  | Probe | 5'-GACGCGGAGTCGAGGTATGCC/3C6/ (SEQ ID NO: 6) |
| CYP24A1 | Forward Primer | 5'-CTTCAACTGCATTTGGCTCTTTG (SEQ ID NO: 7) |
|  | Reverse Primer | 5'-TGTGGCCTGGATGTCGT (SEQ ID NO: 8) |
|  | Probe | 5'-CCACGGACGGTTGGATTGTCC/3C6/ (SEQ ID NO: 9) |
| FA483A | Forward Primer | 5'-TGGAGATTTGTCCTGTCTGGATC (SEQ ID NO: 10) |
|  | Reverse Primer | 5'-CTTGGAGAGGATGTTCCGGT (SEQ ID NO: 11) |
|  | Probe | 5'-CCACGGACGCTTACAGCTTCA/3C6/ (SEQ ID NO: 12) |
| GAGE12D | Forward Primer | 5'-AGGGAGCATCTGCAGGTC (SEQ ID NO: 13) |
|  | Reverse Primer | 5'-CCTGTTCCTGGCTATGAGCTTC (SEQ ID NO: 14) |
|  | Probe | 5'-CGCCGAGGCAAGGGCCGAAG/3C6/ (SEQ ID NO: 15) |
| LRG1 | Forward Primer | 5'-GAGCAGACAGCGACCAAA (SEQ ID NO: 16) |
|  | Reverse Primer | 5'-CAGGAACAGAGTTCTAGAAACATGG (SEQ ID NO: 17) |
|  | Probe | 5'-CCACGGACGAAAGCCCAGGGG/3C6/ (SEQ ID NO: 18) |
| MAGEA4 | Forward Primer | 5'-AGAGGAGCACCAAGGAGAAGA (SEQ ID NO: 19) |
|  | Reverse Primer | 5'-GGCAAAAGCTGGGCAATGG (SEQ ID NO: 20) |
|  | Probe | 5'-CGCCGAGGATCTGCCTGTGG/3C6/ (SEQ ID NO: 21) |
| SFTPB | Forward Primer | 5'-GTCATCGACTACTTCCAGAACC (SEQ ID NO: 22) |
|  | Reverse Primer | 5'-AGGTGCATACAGATGCCG (SEQ ID NO: 23) |
|  | Probe | 5'-CGCCGAGGCAGACTGACTCA/3C6/ (SEQ ID NO: 24) |
| XAGE1D | Forward Primer | 5'-CCCAGGTGCTGGGAAGG (SEQ ID NO: 25) |
|  | Reverse Primer | 5'-ACTGATGCAGCTCTTGCAGA (SEQ ID NO: 26) |
|  | Probe | 5'-CCACGGACGGGAAATGCGCGA/3C6/ (SEQ ID NO: 27) |

FIG. 3 shows exemplary standard curves for LRG-1 RNA at dilutions A-E, i.e., 10 to 100,000 copies per reaction of input RNA, in the RT-QuARTS assay as described above. The average number of RNA strands present as calculated from the fluorescence signal during amplification are shown under "Calc. Strands/Rxn" on the right half of panel A. The graph in panel C shows the fluorescence signal accumulation by cycle number for the reactions having the different indicated amounts of input RNA.

RT-QuARTs Quantitative Data Analysis for Marker Detection

Strand values for individual markers from the samples were determined by using the standard curves for each marker, as discussed above for the LRG-1 RNA. The strand numbers were divided by the CASC3 reference marker strand numbers determined in the same assay well to normalize for varying input RNA amounts. The resulting ratio was multiplied by 100 to generate the "% MARKER" value for each mRNA as shown in FIG. 4.

Receiver operating characteristic (ROC) curves were generated for different groupings of markers using JMP 11.0 software (SAS). The positive percent agreement (diagnostic sensitivity) was calculated by dividing the detected positives by the known lung cancer samples and multiplying by 100, and the negative percent agreement (diagnostic specificity) by dividing the detected negatives by the known normal controls and multiplying by 100.

Figure 4:
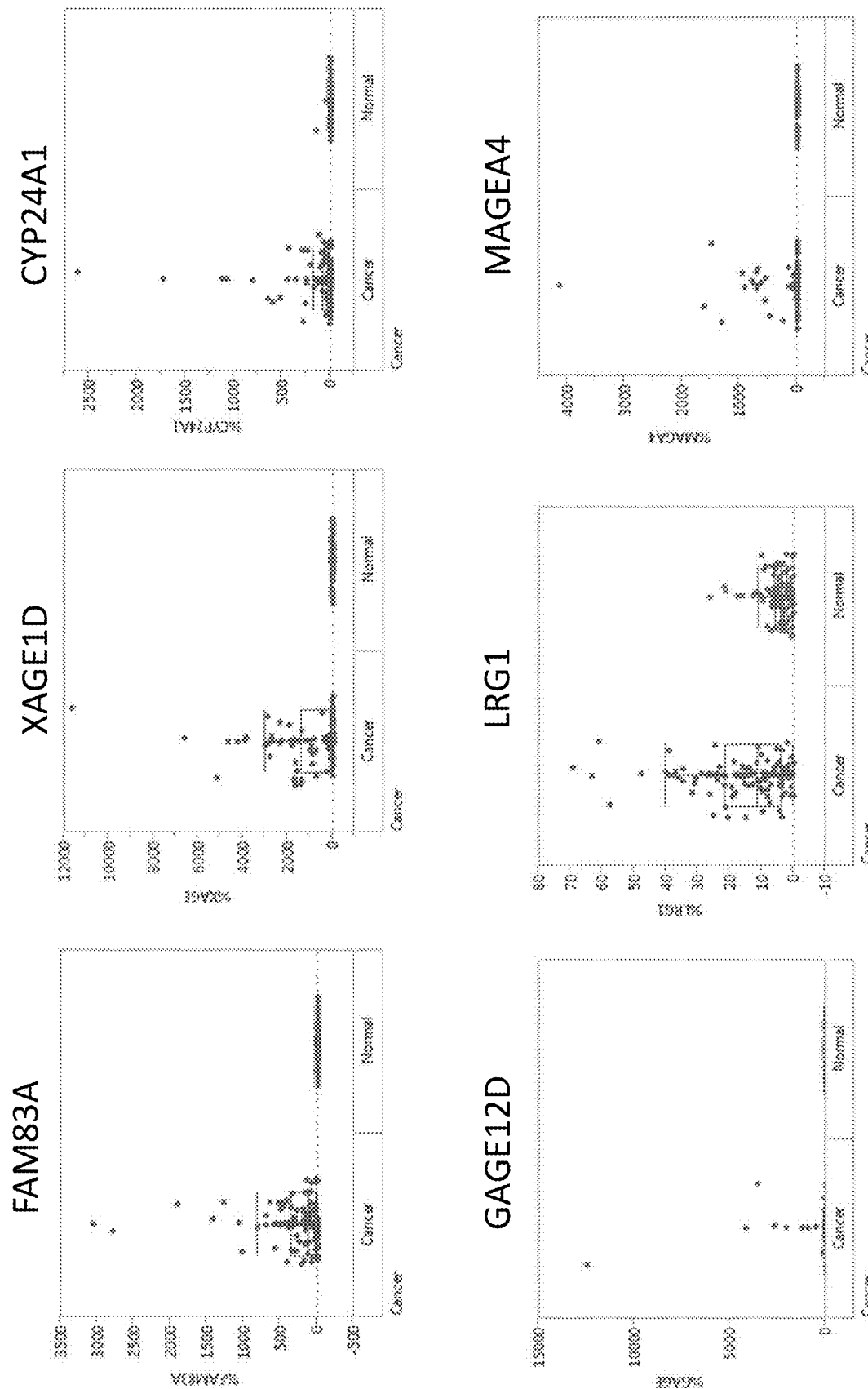
FIG. 4 compares the signals measured for markers FAM83A, XAGE1D, CYP24A1, GAGE12D, LRG1, and MAGEA4 in cancer and normal tissue samples, as described below.

FIG. 4 shows the signal measured from individual marker RNAs from cancer and normal samples. FIG. 5 shows the aggregate sensitivity and specificity for samples analyzed using the indicated combinations of mRNA markers.

Target mRNA sequences (showing T nucleotides in place of U nucleotides) are as follows:

```
AKAP4
>gi|21493038|ref|NM_139289.1| Homo sapiens A kinase (PRKA)
anchor protein 4 (AKAP4), transcript variant 2, mRNA
                                          (SEQ ID NO: 28)
CAGGGGTGGCAGCCAACTGCAGGTGCCCAAGAACTTGGCACTTCTCAGTTCCATCTAAAGGGGC

ACATCTCCCTTCTGGGTGTCACGTTTTCAGCCAAACATCTAAAAGAACTTCATCATCAAGATGT

CTGATGATATTGACTGGTTACGCAGCCACAGGGGTGTGTGCAAGGTAGATCTCTACAACCCAGA

AGGACAGCAAGATCAGGACCGGAAAGTGATATGCTTTGTCGATGTGTCCACCCTGAATGTAGAA

GATAAAGATTACAAGGATGCTGCTAGTTCCAGCTCAGAAGGCAACTTAAACCTGGGAAGTCTGG

AAGAAAAAGAGATTATCGTGATCAAGGACACTGAGAAGAAAGACCAGTCTAAGACAGAGGGATC

TGTATGCCTTTTCAAACAAGCTCCCTCTGATCCTGTAAGTGTCCTCAACTGGCTTCTCAGTGAT

CTCCAGAAGTATGCCTTGGGTTTCCAACATGCACTGAGCCCCTCAACCTCTACCTGTAAACATA

AAGTAGGAGACACAGAGGGCGAATATCACAGAGCATCCTCTGAGAACTGCTACAGTGTCTATGC

CGATCAAGTGAACATAGATTATTTGATGAACAGACCTCAAAACCTACGTCTAGAAATGACAGCA

GCTAAAAACACCAACAATAATCAAAGTCCTTCAGCTCCTCCAGCCAAACCTCCTAGCACTCAGA

GAGCAGTCATTTCCCCTGATGGAGAATGTTCTATAGATGACCTTTCCTTCTACGTCAACCGACT

ATCTTCTCTGGTAATCCAGATGGCCCATAAGGAAATCAAGGAGAAGTTGGAAGGTAAAAGCAAA

TGCCTTCATCATTCAATCTGTCCATCCCCTGGGAACAAAGAGAGAATCAGTCCCCGAACTCCTG

CGAGCAAGATTGCTTCTGAAATGGCCTATGAAGCTGTGGAACTGACAGCTGCAGAAATGCGTGG

CACTGGAGAGGAGTCCAGGGAAGGTGGCCAGAAAAGCTTTCTATATAGCGAATTATCCAACAAG

AGCAAAAGTGGAGACAAACAGATGTCCCAGAGAGAGAGCAAAGAATTTGCAGATTCCATCAGCA

AGGGGCTCATGGTTTATGCAAATCAGGTGGCATCTGACATGATGGTCTCTCTCATGAAGACCTT

GAAAGTGCACAGCTCTGGGAAGCCAATTCCAGCATCTGTGGTCCTGAAGAGGGTGTTGCTAAGG

CACACCAAGGAGATTGTGTCCGATTTGATTGATTCTTGCATGAAGAACCTGCATAATATTACTG

GGGTCCTGATGACTGACTCAGACTTTGTCTCAGCTGTCAAGAGAAATCTGTTCAACCAGTGGAA

ACAAAATGCTACAGACATCATGGAGGCCATGCTGAAGCGCTTGGTCAGTGCCCTTATAGGTGAG

GAGAAGGAGACTAAGTCTCAGAGTCTGTCATATGCATCTTTAAAAGCTGGGTCCCATGATCCCA

AATGCAGGAATCAGAGTCTTGAATTCTCCACCATGAAAGCTGAAATGAAAGAGAGGGACAAAGG

CAAAATGAAATCAGACCCATGCAAGTCACTGACTAGTGCTGAGAAAGTCGGTGAACACATTCTC

AAAGAGGGCCTAACCATCTGGAACCAAAAGCAAGGAAACTCATGCAAGGTGGCTACCAAAGCAT

GCAGCAATAAAGATGAGAAAGGAGAAAAGATCAATGCTTCCACAGATTCACTGGCCAAGGACCT

GATTGTCTCTGCCCTTAAGCTGATCCAGTACCATCTGACCCAGCAGACTAAGGGCAAAGATACA
```

-continued

```
TGTGAAGAAGACTGTCCTGGTTCCACCATGGGCTATATGGCTCAGAGTACTCAATATGAAAAGT

GTGGAGGTGGCCAAAGTGCCAAAGCACTTTCAGTGAAACAACTAGAATCTCACAGAGCCCCTGG

ACCATCCACCTGTCAAAAGGAGAACCAACACCTGGACTCCCAGAAAATGGATATGTCAAACATC

GTTCTAATGCTGATTCAGAAACTGCTTAATGAGAACCCCTTCAAATGTGAGGATCCATGCGAAG

GTGAGAACAAGTGTTCTGAGCCCAGGGCAAGCAAAGCAGCTTCCATGTCCAACAGATCTGACAA

AGCGGAAGAACAATGCCAGGAGCATCAAGAACTTGACTGTACCAGTGGGATGAAGCAAGCGAAC

GGGCAATTTATAGATAAACTAGTAGAATCTGTGATGAAGCTCTGCCTTATCATGGCTAAGTATA

GCAACGATGGGGCAGCCCTTGCTGAGTTGGAAGAACAAGCAGCCTCGGCAAATAAGCCCAATTT

CAGGGGCACCAGATGCATTCACAGTGGTGCAATGCCACAGAACTATCAAGACTCTCTTGGACAT

GAAGTAATTGTCAATAATCAGTGCTCTACAAATAGCTTGCAGAAGCAGCTCCAGGCTGTCCTGC

AGTGGATTGCAGCCTCCCAGTTTAACGTGCCCATGCTCTACTTCATGGGAGATAAGGATGGACA

ACTGGAAAAGCTTCCTCAGGTTTCAGCTAAAGCAGCAGAGAAGGGGTACAGTGTAGGAGGTCTT

CTTCAAGAGGTCATGAAGTTTGCCAAGGAACGGCAACCAGATGAAGCTGTGGGAAAGGTGGCCA

GGAAACAGTTGCTGGACTGGCTGCTCGCTAACCTGTGAGCTGATCCTTGACTCCTCTTCATCTT

AGCCCCCCTAGCAGCATTCCATCCCAGCCAGAGCACCCCCACCATCAGGCCAGTCAACTGCACA

ATACACAACTGTATTTCCCAATACACTTGAGCAGTTGCCTGTGAATGTAAGAGGTGTCAACAAA

CTGGGAAATAAAATAAAAAAAATAATAAAAAAAAAAAAAAAAAAAAA
```

CASC3
>gi|102468569|ref|NM_007359.4| Homo sapiens cancer susceptibility candidate 3 (CASC3), mRNA (SEQ ID NO: 29)

```
AATCCGGGTCGGCCGCAAACGTGCCGCAGGCCTAGGCCCCGCCCAGTGCCCCGCCCCTCCCCA

ACACACACACACACACACACACACACACACCCAACACACACACACACACCCCAACACACAC

ACACACACACACACACACACACACACACACACACACACACACAGCGGGATGGCCGAGC

GCCGCACGCGTAGCACGCCGGGACTAGCTATCCAGCCTCCCAGCAGCCTCTGCGACGGGCGCGG

TGCGTAAGTACCTCGCCGGTGGTGGCCGTTCTCCGTAAGATGGCGGACCGGCGGCGGCAGCGCG

CTTCGCAAGACACCGAGGACGAGGAATCTGGTGCTTCGGGCTCCGACAGCGGCGGCTCCCCGTT

GCGGGGAGGCGGGAGCTGCAGCGGTAGCGCCGGAGGCGGCGGCAGCGGCTCTCTGCCTTCACAG

CGCGGAGGCCGAACCGGGGCCCTTCATCTGCGGCGGGTGGAGAGCGGGGCGCCAAGAGTGCTG

AGGAGTCGGAGTGTGAGAGTGAAGATGGCATTGAAGGTGATGCTGTTCTCTCGGATTATGAAAG

TGCAGAAGACTCGGAAGGTGAAGAAGGTGAATACAGTGAAGAGGAAAACTCCAAAGTGGAGCTG

AAATCAGAAGCTAATGATGCTGTTAATTCTTCAACAAAAGAAGAGAAGGGAGAAGAAAAGCCTG

ACACCAAAAGCACTGTGACTGGAGAGAGGCAAAGTGGGGACGGACAGGAGAGCACAGAGCCTGT

GGAGAACAAAGTGGGTAAAAAGGGCCCTAAGCATTTGGATGATGATGAAGATCGGAAGAATCCA

GCATACATACCTCGGAAAGGGCTCTTCTTTGAGCATGATCTTCGAGGGCAAACTCAGGAGGAGG

AAGTCAGACCCAAGGGGCGTCAGCGAAAGCTATGGAAGGATGAGGGTCGCTGGGAGCATGACAA

GTTCCGGGAAGATGAGCAGGCCCCAAAGTCCCGACAGGAGCTCATTGCTCTTTATGGTTATGAC

ATTCGCTCAGCTCATAATCCTGATGACATCAAACCTCGAAGAATCCGGAAACCCCGATATGGGA

GTCCTCCACAAAGAGATCCAAACTGGAACGGTGAGCGGCTAAACAAGTCTCATCGCCACCAGGG

TCTTGGGGGCACCCTACCACCAAGGACATTTATTAACAGGAATGCTGCAGGTACCGGCCGTATG

TCTGCACCCAGGAATTATTCTCGATCTGGGGCTTCAAGGAAGGTCGTGCTGGTTTTAGGCCTG

TGGAAGCTGGTGGGCAGCATGGTGGCCGGTCTGGTGAGACTGTTAAGCATGAGATTAGTTACCG
```

-continued

```
GTCACGGCGCCTAGAGCAGACTTCTGTGAGGGATCCATCTCCAGAAGCAGATGCTCCAGTGCTT

GGCAGTCCTGAGAAGGAAGAGGCAGCCTCAGAGCCACCAGCTGCTGCTCCTGATGCTGCACCAC

CACCCCCTGATAGGCCCATTGAGAAGAAATCCTATTCCCGGGCAAGAAGAACTCGAACCAAAGT

TGGAGATGCAGTCAAGCTTGCAGAGGAGGTGCCCCCTCCTCCTGAAGGACTGATTCCAGCACCT

CCAGTCCCAGAAACCACCCCAACTCCACCTACTAAGACTGGGACCTGGGAAGCTCCGGTGGATT

CTAGTACAAGTGGACTTGAGCAAGATGTGGCACAACTAAATATAGCAGAACAGAATTGGAGTCC

GGGGCAGCCTTCTTTCCTGCAACCACGGGAACTTCGAGGTATGCCCAACCATATACACATGGGA

GCAGGACCTCCACCTCAGTTTAACCGGATGGAAGAAATGGGTGTCCAGGGTGGTCGAGCCAAAC

GCTATTCATCCCAGCGGCAAAGACCTGTGCCAGAGCCCCCGCCCCTCCAGTGCATATCAGTAT

CATGGAGGGACATTACTATGATCCACTGCAGTTCCAGGGACCAATCTATACCCATGGTGACAGC

CCTGCCCCGCTGCCTCCACAGGGCATGCTTGTGCAGCCAGGAATGAACCTTCCCCACCCAGGTT

TACATCCCCACCAGACACCAGCTCCTCTGCCCAATCCAGGCCTCTATCCCCCACCAGTGTCCAT

GTCTCCAGGACAGCCACCACCTCAGCAGTTGCTTGCTCCTACTTACTTTTCTGCTCCAGGCGTC

ATGAACTTTGGTAATCCCAGTTACCCTTATGCTCCAGGGGCACTGCCTCCCCCACCACCGCCTC

ATCTGTATCCTAATACACAGGCCCCATCACAGGTATATGGAGGAGTGACCTACTATAACCCCGC

CCAGCAGCAGGTGCAGCCAAAGCCCTCCCCACCCCGGAGGACTCCCCAGCCAGTCACCATCAAG

CCCCCTCCACCTGAGGTTGTAAGCAGGGGTTCCAGTTAATACAAGTTTCTGAATATTTTAAATC

TTAACATCATATAAAAAGCAGCAGAGGTGAGAACTCAGAAGAGAAATACAGCTGGCTATCTACT

ACCAGAAGGGCTTCAAAGATATAGGGTGTGGCTCCTACCAGCAAACAGCTGAAAGAGGAGGACC

CCTGCCTTCCTCTGAGGACAGGCTCTAGAGAGAGGGAGAAACAAGTGGACCTCGTCCCATCTTC

ACTCTTCACTTGAGTTGGCTGTGTTCGGGGGAGCAGAGAGAGCCAGACAGCCCCAAGCTTCTGA

GTCTAGATACAGAAGCCCATGTCTTCTGCTGTTCTTCACTTCTGGGAAATTGAAGTGTCTTCTG

TTCCCAAGGAAGCTCCTTCCTGTTTGTTTTGTTTTCTAAGATGTTCATTTTTAAAGCCTGGCTT

CTTATCCTTAATATTATTTTAATTTTTTCTCTTTGTTTCTGTTTCTTGCTCTCTCCCTGCCT

TTAAATGAAACAAGTCTAGTCTTCTGGTTTTCTAGCCCCTCTGGATTCCCTTTTGACTCTTCCG

TGCATCCCAGATAATGGAGAATGTATCAGCCAGCCTTCCCCACCAAGTCTAAAAAGACCTGGCC

TTTCACTTTTAGTTGGCATTTGTTATCCTCTTGTATACTTGTATTCCCTTAACTCTAACCCTGT

GGAAGCATGGCTGTCTGCACAGAGGGTCCCATTGTGCAGAAAAGCTCAGAGTAGGTGGGTAGGA

GCCCTTCTCTTTGACTTAGGTTTTTAGGAGTCTGAGCATCCATCAATACCTGTACTATGATGGG

CTTCTGTTCTCTGCTGAGGGCCAATACCCTACTGTGGGGAGAGATGGCACACCAGATGCTTTTG

TGAGAAAGGGATGGTGGAGTGAGAGCCTTTGCCTTTAGGGGTGTGTATTCACATAGTCCTCAGG

GCTCAGTCTTTTGAGGTAAGTGGAATTAGAGGGCCTTGCTTCTCTTCTTTCCATTCTTCTTGCT

ACACCCCTTTTCCAGTTGCTGTGGACCAATGCATCTCTTTAAAGGCAAATATTATCCAGCAAGC

AGTCTACCCTGTCCTTTGCAATTGCTCTTCTCCACGTCTTTCCTGCTACAAGTGTTTTAGATGT

TACTACCTTATTTTCCCCGAATTCTATTTTTGTCCTTGCAGACAGAATATAAAAACTCCTGGGC

TTAAGGCCTAAGGAAGCCAGTCACCTTCTGGGCAAGGGCTCCTATCTTTCCTCCCTATCCATGG

CACTAAACCACTTCTCTGCTGCCTCTGTGGAAGAGATTCCTATTACTGCAGTACATACGTCTGC

CAGGGGTAACCTGGCCACTGTCCCTGTCCTTCTACAGAACCTGAGGGCAAAGATGGTGGCTGTG

TCTCTCCCCGGTAATGTCACTGTTTTTATTCCTTCCATCTAGCAGCTGGCCTAATCACTCTGAG

TCACAGGTGTGGGATGGAGAGTGGGGAGAGGCACTTAATCTGTAACCCCCAAGGAGGAAATAAC

TAAGAGATTCTTCTAGGGGTAGCTGGTGGTTGTGCCTTTTGTAGGCTGTTCCCTTTGCCTTAAA
```

-continued

CCTGAAGATGTCTCCTCAAGCCTGTGGGCAGCATGCCCAGATTCCCAGACCTTAAGACACTGTG

AGAGTTGTCTCTGTTGGTCCACTGTGTTTAGTTGCAAGGATTTTTCCATGTGTGGTGGTGTTTT

TTGTTACTGTTTTAAAGGGTGCCCATTTGTGATCAGCATTGTGACTTGGAGATAATAAAATTTA

GACTATAAACTTGGCTCCCTAAAAAAAAAAAAAAAAAA

CYP24A1
>gi|193083115|ref|NM_000782.4| *Homo sapiens* cytochrome P450,
family 24, subfamily A, polypeptide 1 (CYP24A1), transcript
variant 1, mRNA (SEQ ID NO: 30)

GACAGGAGGAAACGCAGCGCCAGCAGCATCTCATCTACCCTCCTTGACACCTCCCCGTGGCTCC

AGCCAGACCCTAGAGGTCAGCCTTGCGGACCAACAGGAGGACTCCCAGCTTTCCCTTTTCAAGA

GGTCCCCAGACACCGGCCACCCTCTTCCAGCCCCTGCGGCCAGTGCAAGGAGGCACCAATGCTC

TGAGGCTGTCGCGTGGTGCAGCGTCGAGCATCCTCGCCGAGGTCCTTTCTGCTGCCTGTCCCGC

CTCACCCCGCTCCATCACACCAGCTGGCCCTCTTTGCTTCCTTTTCCCAGAATCGTTAAGCCCC

GACTCCCACTAGCACCTCGTACCAACCTCGCCCCACCCCATCCTCCTGCCTTCCCGCGCTCCGG

TGTCCCCCGCTGCCATGAGCTCCCCCATCAGCAAGAGCCGCTCGCTTGCCGCCTTCCTGCAGCA

GCTGCGCAGTCCGAGGCAGCCCCCGAGACTGGTGACATCTACGGCGTACACGTCCCCTCAGCCG

CGAGAGGTGCCAGTCTGCCCGCTGACAGCTGGTGGCGAGACTCAGAACGCGGCCGCCCTGCCGG

GCCCCACCAGCTGGCCACTGCTGGGCAGCCTGCTGCAGATTCTCTGGAAAGGGGGTCTCAAGAA

ACAGCACGACACCCTGGTGGAGTACCACAAGAAGTATGGCAAGATTTTCCGCATGAAGTTGGGT

TCCTTTGAGTCGGTGCACCTGGGCTCGCCATGCCTGCTGGAAGCGCTGTACCGCACCGAGAGCG

CGTACCCGCAGCGGCTGGAGATCAAACCGTGGAAGGCCTATCGCGACTACCGCAAAGAAGGCTA

CGGGCTGCTGATCCTGGAAGGGGAAGACTGGCAGCGGGTCCGGAGTGCCTTTCAAAAGAAACTA

ATGAAACCAGGGGAAGTGATGAAGCTGGACAACAAAATCAATGAGGTCTTGGCCGATTTTATGG

GCAGAATAGATGAGCTCTGTGATGAAAGAGGCCACGTTGAAGACTTGTACAGCGAACTGAACAA

ATGGTCGTTTGAAAGTATCTGCCTCGTGTTGTATGAGAAGAGATTTGGGCTTCTCCAGAAGAAT

GCAGGGGATGAAGCTGTGAACTTCATCATGGCCATCAAAACAATGATGAGCACGTTTGGGAGGA

TGATGGTCACTCCAGTCGAGCTGCACAAGAGCCTCAACACCAAGGTCTGGCAGGACCACACTCT

GGCCTGGGACACCATTTTCAAATCAGTCAAAGCTTGTATCGACAACCGGTTAGAGAAGTATTCT

CAGCAGCCTAGTGCAGATTTCCTTTGTGACATTTATCACCAGAATCGGCTTTCAAAGAAAGAAT

TGTATGCTGCTGTCACAGAGCTCCAGCTGGCTGCGGTGGAAACGACAGCAAACAGTCTAATGTG

GATTCTCTACAATTTATCCCGTAATCCCCAAGTGCAACAAAAGCTTCTTAAGGAAATTCAAAGT

GTATTACCTGAGAATCAGGTGCCACGGGCAGAAGATTTGAGGAATATGCCGTATTTAAAAGCCT

GTCTGAAAGAATCTATGAGGCTTACGCCGAGTGTACCATTTACAACTCGGACTCTTGACAAGGC

AACAGTTCTGGGTGAATATGCTTTACCCAAAGGAACAGTGCTCATGCTAAATACCCAGGTGTTG

GGATCCAGTGAAGACAATTTTGAAGATTCAAGTCAGTTTAGACCTGAACGTTGGCTTCAGGAGA

AGGAAAAAATTAATCCTTTTGCGCATCTTCCATTTGGCGTTGGAAAAAGAATGTGCATTGGTCG

CCGATTAGCAGAGCTTCAACTGCATTTGGCTCTTTGTTGGATTGTCCGCAAATACGACATCCAG

GCCACAGACAATGAGCCTGTTGAGATGCTACACTCAGGCACCCTGGTGCCCAGCCGGGAACTCC

CCATCGCGTTTTGCCAGCGATAATACGCCTCAGATGGTGGTATTTGCTAACATCATATCCAACT

CAGGGAAGCGGACTGAGTGCTGGGATCCAAGGCATTCTACAGGGTTCACTGCTGGTTTACACTT

CACCTGTGTCAGCACCATCTTCAGGTGCTTAGAATGGCCTGGGAGCCTGTTCTGTCTTGCATCT

TCCATGACATGAAAGGGAGGCTGGCACTTGTCAGTCAGGTAGAGGTTACAAACCGTTTCAGGCC

-continued

```
CTGCCTACCACATTCACTGTTTGAATCTTTAATTCCCAAGAATAAGTTTACATTTCACAATGAA

TGACCTACAACAGCTAAATTTTCTGGGGCTGGGAGTAATACTGACAATCCATTTACTGTAGCTC

TGCTTAATGTACTACTTAGGAAAATGTCCCTGCTTAATAATGTAAGCCAAGCTAAATGATGGTT

AAAGTTATCAGGCCTCCCATGAAATTGCGTTCTTCCTGCATTGAAATAAAAACATTATTGGGAA

ACTAGAGAACACCTCTATTTTTAAAAGGACTTTAACGAAGTCAAACAACTTATAAGACTAGTGA

TTCACTGGGGCATTATTTTGTTAGAGGACCTTAAAATTGTTTATTTTTTAAATGTGATTCCTTT

ATGGCATTAGGGTAAAGATGAAGCAATAATTTTTAAATTGTGTATGTGCATATGAAGCACAGAC

ATGCATGTGTGTGTGTCTGTGTGTGTGTCCGTGTATGTGTGTGGGTTCTAATGGTAAT

TTGCCTCAGTCATTTTTTAATATTTGCAGTACTTGATTTAGGATCTGTGGTGCAGGGCAATGT

TTCAAAGTTTAGTCACAGCTTAAAAACATTCAGTGTGACTTTAATATTATAAAATGATTTCCCA

TGCCATAATTTTTCTGTCTATTAAATGGGACAAGTGTAAAGCATGCAAAAGTTAGAGATCTGTT

ATATAACATTTGTTTTGTGATTTGAACTCCTAGGAAAAATATGATTTCATAAATGTAAAATGCA

CAGAAATGCATGCAATACTTATAAGACTTAAAAATTGTGTTTACAGATGGTTTATTTGTGCATA

TTTTTACTACTGCTTTTCCTAAATGCATACTGTATATAATTCTGTGTATTTGATAAATATTTCT

TCCTACATTATATTTTTAGAATATTTCAGAAATATACATTTATGTCTTTATATTGTAATAAATA

TGTACATATCTAGGTATATGCTTTCTCTCTGCTGTGAAATTATTTTTAGAATTATAAATTCACG

TCTTGTCAGATTTCATCTGTATACCTTCAAATTCTCTGAAAGTAAAAATAAAAGTTTTTAAATA

TTAAAAAAAAAAAAAAAAAAAA

FAM83A
>gi|767953716|ref|XM005251087.2| PREDICTED: Homo sapiens family
with sequence similarity 83, member A (FAM83A), transcript
variant X1, mRNA
                                                 (SEQ ID NO: 31)
AGGAAATATCCCATGGCTGACTGTGCCAAGGAGGTGTCTGAGCCAGCCCTCCCGGCCCGAGGGC

AGGGCAGGTGGCCCTGAGAGATAAGCCAATCCCGCAGCTGCAGATGAGGAGTTCTGAGAAGCAT

TGCTCAGGACAGCGGTAAATCACTTCTTGGAGGTGCCCTGCACGCCGGTCCTGGGAGCAGGCGG

CCTCCCGGGGGTGCGGGAGCCCCACTCCTCCGTGGTGTGTTCCATTTGCTTCCCACATCTGGAG

GAGCTGACGTGCCAGCCTCCCCCAGCACCACCCAGGGACGGGAGGCATGAGCCGGTCAAGGCAC

CTGGGCAAAATCCGGAAGCGTCTGGAAGATGTCAAGAGCCAGTGGGTCCGGCCAGCCAGGGCTG

ACTTTAGTGACAACGAGAGTGCCCGGCTGGCCACGGACGCCCTCTTGGATGGGGGTTCTGAAGC

CTACTGGCGGGTGCTCAGCCAGGAAGGCGAGGTGGACTTCTTGTCCTCGGTGGAGGCCCAGTAC

ATCCAGGCCCAGGCCAGGGAGCCCCCGTGTCCCCCAGACACCCTGGGAGGGGCGGAAGCAGGCC

CTAAGGGACTGGACTCCAGCTCCCTACAGTCCGGCACCTACTTCCCTGTGGCCTCAGAGGGCAG

CGAGCCGGCCCTACTGCACAGCTGGGCCTCAGCTGAGAAGCCCTACCTGAAGGAAAAATCCAGC

GCCACTGTGTACTTCCAGACCGTCAAGCACAACAACATCAGAGACCTCGTCCGCCGCTGCATCA

CCCGGACTAGCCAGAACATTTCCATCCGGAGTGTGGAAGGAGAGATATACTGTGCCAAGTCAGG

CAGGAAATTCGCTGGCCAAATCCGGGAGAAGTTCATCATCTCGGACTGGAGATTTGTCCTGTCT

GGATCTTACAGCTTCACCTGGCTCTGCGGACACGTGCACCGGAACATCCTCTCCAAGTTCACAG

GCCAGGCGGTGGAGCTGTTTGACGAGGAGTTCCGCCACCTCTACGCCTCCTCCAAGCCTGTGAT

GGGCCTGAAGTCCCCGCGGCTGGTCGCCCCCGTCCCGCCCGGAGCAGCCCCGGCCAATGGCCGC

CTTAGCAGCAGCAGTGGCTCCGCCAGTGACCGCACGTCCTCCAACCCCTTCAGCGGCCGCTCGG

CAGGCAGCCACCCCGGTACCCGAAGTGTGTCCGCGTCTTCAGGGCCCTGTAGCCCCGCGGCCCC

ACACCCGCCTCCACCGCCCCGGTTCCAGCCCCACCAAGGCCCTTGGGGAGCCCCGAGTCCCCAG
```

-continued

```
GCCCACCTCTCCCCGCGGCCCCACGACGGCCCGCCCGCCGCTGTCTACAGCAACCTGGGGCCT

ACAGGCCCACGCGGCTGCAGCTGGAGCAGCTGGGCCTGGTGCCGAGGCTGACTCCAACCTGGAG

GCCCTTCCTGCAGGCCTCCCCTCACTTCTGAAGGTCCCATCCCCTGCTGCCCTCCGCAGGCCCA

GGGCTGGGCACTCCCTGAGACCCAAAGACCCACCTCAACGACGAGTGGCGTTGAGCCACTTCCC

TTTGAAAAGACACTCAAAATCACTGCCATGGTTCAATGTTCCCAGGCCCCAGGCCATCCACTTG

CCGGCCCCCACCAGTTCTTGGGTTCCCCGCTCTAGTTTGACCTGTGCAGCACATTCCAGAAGGT

TCCAGGGAGGTTGTGGGGCAGCTAGAGGACAAAATCATGAAAACAGAGTCCCTGTCTTCCAGAG

ATCATCCGGGGCTTTAATATTAATGGCCCCCAAAACTCCGTAAGAAGCAGGAAATGCAGCCCAA

GTTTTACAAATGGGTAAACAGAGGCACTGAGAGATAGATGGTAGTTTGGTACTTCTGGTTCCCA

GTGCCCAGGAATGGTCCACTCCCAAGAAATTCAGGAAAGAAAGACTGAGGAGAAGGTGTGGGAA

CATTCTGGATGTTTCGGGAGAGTTGGGGAAACTCCTCCTCTTAGGAAAGGCTAATACTAGGGTA

TCCTTGGGCCCAATGAATTAGGGGTGAGGCCCCAGAACCCGTTATCTATGAGTTGTATGGGGGA

GCCATCTGAAGCTGTAGCCACCAGGGATGCAGCTAGCTGAGGAGTTTGGGGTGTTGGGTTGGAC

AAGGCAGGTTAGTAGACTCAGATTCTTGCTTCAAAGAGCCTTGGGCTGGCCTGGAGGTCCCTGG

AGTCTAGACTGGACCTAGGAGCTTGAGTTGTCAGGGGCCAGGACTGGCCCCACTGCAGTGCCCA

GGCCAGTCTTGAGCAGCAGGGAGGGCTCAGCTGTCCCCAGATCCAGGTGCCTCTGACCAGCCTG

GTCACCTCCTGAGGAATAAATGCTGAACCTCACAAGCCCCATCATTCATTTCTTCTCAATTCAC

AGTGCCCCTCTTTGTTTCTGGGGTGGAACTAGGTCCTGAGGGCACAGCCTAGCTGAGTGCAAAG

AAATATAGGATGCTTAGAAAGCATACAGGAGGGGCCAGGCGTGGTGGCTCATGCCTGTAATCCC

AGAACTTTGGGATGCCAAGGTGGTTGGATTACCTGAGATCAGGTGGATTACCTGGTCTCGAGAC

CAGCCTGACCAATATGGTGAAACCCCGTCTCTACTAAAAATACAAAAATTAGGCTGAGACAGGA

GAATTGCTTGAACCCAGGAAGCAGAGGTTGCAATGAGCTGAGATTGCATCACTGCACTCCAGCA

TGGGCAACAAAGCAAGACTCCGTCACAGAAAAAAAAAAAAAAAAGAGAGAGAGCATAGAGGAGG

GTTGGCCAGCCCTGTGGTGGGTGGGATGTCAGAGACACTTCCCAGATAAAGTAAGAGTTAACCC

TGCACCTCAGGTGTGATAGTGGGGTCAGTGGTATGTGATCCAGGCTGGGGAGCCAGAGGGGAGC

AGGTGCCAACTCCACATCCTTCTCCTGTTTCTAGGCCCTCTCCTCCCTTGTCGGTTTTTGGCGG

GGAAGCTCAGCCTTCGCTGTGGAGGGACGAGAGCACAGAGCTCTTCCTCCTGGTGGCCTCTGAC

CCCTGACGGCCTGTGGCATCCTCCCTAGTCCCCTCTGCCCATCCATCCCTCTGTTCCAATTCTC

CACTGCTCCCAGCATGATCTGGGGCATCTTGGCTTCTGGTTTCTTTTATTATTATTATTATTAT

TAATTATTGTATTCCTGTCCTTCACTTTTTTCCTCCTTAGTTCCTGAAAGTAAACAAAACAAAA

CAAAAACAAAAAAACAAACAACACTTTGGTTCCTGATGGCTTTCTGAACCCAGCCCTGACCTTG

TTGTTTCACAGCTGACGGCTGAGATGAGGTTAGAATGACTGGGCCCGGCTGAACATTCCAAATT

GGATTTCACCATCTGCTGAGAAAGTTTAAGGAAGGCAAAGCTTGCCAGGTCACAGAAGCTCCCA

AGCCCAGCTTTCCAAAGGCCTCAGCCTGTGCCTGTGTCGAGCTCAGTCCTGGGAGATAGGGGAG

AACCTGCAGGCAGGAACAAGCCCCCCTACTCCTGACCACCCTCCATCAGCAGTCTCCCCTCCGT

GGTCGTCTTTGTTGACAAAGGTGCAGTTTCTCCTCTCCTGGGCACCTGTAACATGTGATGCGCT

GCCTGCTGGGAGGTTAGGTCGGGGCTGCCCCGGCGAGTGGAGCATGAGCAGAACCGCCGAGGGT

CACTTCTGGGCAGAAGCTTTGAGAGCCTGGGTCCAGGTTGCCACATAGAAGCAGCTCTCCAGTT

GAAACCCTCCTCTGCCAGCCTGGGGTCCTAAGCGATGAGCAGAATCCCCCACTCCCACCCCACC

AACCCACAATGGATATGTAGTGAGCAAGAAATAAACCTTTGTTGTTTAAGCCA
```

-continued

GAGE12D
gi|187608822|ref|NM_001127199.1| *Homo sapiens* G antigen 12D
(GAGE12D), mRNA (SEQ ID NO: 32)
GTTCACTGGGCGTCTTCTGCCCGGCCCCTTCGCCCACGTGAAGAACGCCAGGGAGCTGTGAGGC

AGTGCTGTGTGGTTCCTGCCGTCCGGACTCTTTTTCCTCTACTGAGATTCATCTGTGTGAAATA

TGAGTTGGCGAGGAAGATCGACCTATTATTGGCCTAGACCAAGGCGCTATGTACAGCCTCCTGA

AATGATTGGGCCTATGCGGCCCGAGCAGTTCAGTGATGAAGTGGAACCAGCAACACCTGAAGAA

GGGGAACCAGCAACTCAATGTCAGGATCCTGCAGCTGCTCAGGAGGGAGAGGATGAGGGAGCAT

CTGCAGGTCAAGGGCCGAAGCCTGAAGCTCATAGCCAGGAACAGGGTCACCCACAGACTGGGTG

TGAGTGTGAAGATGGTCCTGATGGGCAGGAGATGGACCCGCCAAATCCAGAGGAGGTGAAAACG

CCTGAAGAAGGTGAAAAGCAATCACAGTGTTAAAAGAAGACACGTTGAAATGATGCAGGCTGCT

CCTATGTTGGAAATTTGTTCATTAAAATTCTCCCAATAAAGCTTTACAGCCTTCTGCAAAGAAG

TCTTGCGCA

LRG1
gi|49574519|ref|NM_052972.2| *Homo sapiens* leucine-rich alpha-2-
glycoprotein 1 (LRG1), mRNA (SEQ ID NO: 33)
GCAGAGCTACCATGTCCTCTTGGAGCAGACAGCGACCAAAAAGCCCAGGGGGCATTCAACCCCA

TGTTTCTAGAACTCTGTTCCTGCTGCTGCTGTTGGCAGCCTCAGCCTGGGGGGTCACCCTGAGC

CCCAAAGACTGCCAGGTGTTCCGCTCAGACCATGGCAGCTCCATCTCCTGTCAACCACCTGCCG

AAATCCCCGGCTACCTGCCAGCCGACACCGTGCACCTGGCCGTGGAATTCTTCAACCTGACCCA

CCTGCCAGCCAACCTCCTCCAGGGCGCCTCTAAGCTCCAAGAATTGCACCTCTCCAGCAATGGG

CTGGAAAGCCTCTCGCCCGAATTCCTGCGGCCAGTGCCGCAGCTGAGGGTGCTGGATCTAACCC

GAAACGCCCTGACCGGGCTGCCCCCGGGCCTCTTCCAGGCCTCAGCCACCCTGGACACCCTGGT

ATTGAAAGAAAACCAGCTGGAGGTCCTGGAGGTCTCGTGGCTACACGGCCTGAAAGCTCTGGGG

CATCTGGACCTGTCTGGGAACCGCCTCCGGAAACTGCCCCCCGGGCTGCTGGCCAACTTCACCC

TCCTGCGCACCCTTGACCTTGGGGAGAACCAGTTGGAGACCTTGCCACCTGACCTCCTGAGGGG

TCCGCTGCAATTAGAACGGCTACATCTAGAAGGCAACAAATTGCAAGTACTGGGAAAAGATCTC

CTCTTGCCGCAGCCGGACCTGCGCTACCTCTTCCTGAACGGCAACAAGCTGGCCAGGGTGGCAG

CCGGTGCCTTCCAGGGCCTGCGGCAGCTGGACATGCTGGACCTCTCCAATAACTCACTGGCCAG

CGTGCCCGAGGGGCTCTGGGCATCCCTAGGGCAGCCAAACTGGGACATGCGGGATGGCTTCGAC

ATCTCCGGCAACCCCTGGATCTGTGACCAGAACCTGAGCGACCTCTATCGTTGGCTTCAGGCCC

AAAAAGACAAGATGTTTTCCCAGAATGACACGCGCTGTGCTGGGCCTGAAGCCGTGAAGGGCCA

GACGCTCCTGGCAGTGGCCAAGTCCCAGTGAGACCAGGGGCTTGGGTTGAGGGTGGGGGTCTG

GTAGAACACTGCAACCCGCTTAACAAATAATCCTGCCTTTGGCCGGGTGCGGGGGCTCACGCCT

GTAATCCCAGCACTTTGGGAGGCCCAGGTGGCGGATCACGAGGTCAGGAGATCGAGACCATCT

TGGCTAACATGGTGAAACCCTGTCTCTACTAAAAATATAAAAATTAGCCAGGCGTGGTGGTGG

GCACCTGTAGTCCCAGCAACTCGGGAGGCTGAGGCAGGAGAATGGCGTGAACTTGGGAGGCGGA

GCTTGCGGTGAGCCAAGATCGTGCCACTGCACTCTAGCCTGGGCGACAGAGCAAGACTGTCTCA

AAAAAATTAAAATTAAAATTAAAAACAAATAATCCTGCCTTTTACAGGTGAAACTCGGGGCTGT

CCATAGCGGCTGGGACCCCGTTTCATCCATCCATGCTTCCTAGAACACACGATGGGCTTTCCTT

ACCCATGCCCAAGGTGTGCCCTCCGTCTGGAATGCCGTTCCCTGTTTCCCAGATCTCTTGAACT

-continued

CTGGGTTCTCCCAGCCCCTTGTCCTTCCTTCCAGCTGAGCCCTGGCCACACTGGGGCTGCCTTT

CTCTGACTCTGTCTTCCCCAAGTCAGGGGGCTCTCTGAGTGCAGGGTCTGATGCTGAGTCCCAC

TTAGCTTGGGGTCAGAACCAAGGGGTTTAATAAATAACCCTTGAAAACTGGA

MAGEAA
>gi|58530866|ref|NM_001011548.1| *Homo sapiens* MAGE family member
A4 (MAGEA4), transcript variant 1, mRNA
(SEQ ID NO: 34)

AGAGACAAGCGAGCTTCTGCGTCTGACTCGCAGCTTGAGACTGGCGGAGGGAAGCCCGCCCAGG

CTCTATAAGGAGACAAGGTTCTGAGCAGACAGGCCAACCGGAGGACAGGATTCCCTGGAGGCCA

CAGAGGAGCACCAAGGAGAAGATCTGCCTGTGGGTCCCCATTGCCCAGCTTTTGCCTGCACTCT

TGCCTGCTGCCCTGACCAGAGTCATCATGTCTTCTGAGCAGAAGAGTCAGCACTGCAAGCCTGA

GGAAGGCGTTGAGGCCCAAGAAGAGGCCCTGGGCCTGGTGGGTGCACAGGCTCCTACTACTGAG

GAGCAGGAGGCTGCTGTCTCCTCCTCCTCTCCTCTGGTCCCTGGCACCCTGGAGGAAGTGCCTG

CTGCTGAGTCAGCAGGTCCTCCCCAGAGTCCTCAGGGAGCCTCTGCCTTACCCACTACCATCAG

CTTCACTTGCTGGAGGCAACCCAATGAGGGTTCCAGCAGCCAAGAAGAGGAGGGCCAAGCACC

TCGCCTGACGCAGAGTCCTTGTTCCGAGAAGCACTCAGTAACAAGGTGGATGAGTTGGCTCATT

TTCTGCTCCGCAAGTATCGAGCCAAGGAGCTGGTCACAAAGGCAGAAATGCTGGAGAGAGTCAT

CAAAAATTACAAGCGCTGCTTTCCTGTGATCTTCGGCAAAGCCTCCGAGTCCCTGAAGATGATC

TTTGGCATTGACGTGAAGGAAGTGGACCCCGCCAGCAACACCTACACCCTTGTCACCTGCCTGG

GCCTTTCCTATGATGGCCTGCTGGGTAATAATCAGATCTTTCCCAAGACAGGCCTTCTGATAAT

CGTCCTGGGCACAATTGCAATGGAGGGCGACAGCGCCTCTGAGGAGGAAATCTGGGAGGAGCTG

GGTGTGATGGGGGTGTATGATGGGAGGGAGCACACTGTCTATGGGGAGCCCAGGAAACTGCTCA

CCCAAGATTGGGTGCAGGAAAACTACCTGGAGTACCGGCAGGTACCCGGCAGTAATCCTGCGCG

CTATGAGTTCCTGTGGGGTCCAAGGGCTCTGGCTGAAACCAGCTATGTGAAAGTCCTGGAGCAT

GTGGTCAGGGTCAATGCAAGAGTTCGCATTGCCTACCCATCCCTGCGTGAAGCAGCTTTGTTAG

AGGAGGAAGAGGGAGTCTGAGCATGAGTTGCAGCCAGGGCTGTGGGGAAGGGGCAGGGCTGGGC

CAGTGCATCTAACAGCCCTGTGCAGCAGCTTCCCTTGCCTCGTGTAACATGAGGCCCATTCTTC

ACTCTGTTTGAAGAAAATAGTCAGTGTTCTTAGTAGTGGGTTTCTATTTTGTTGGATGACTTGG

AGATTTATCTCTGTTTCCTTTTACAATTGTTGAAATGTTCCTTTTAATGGATGGTTGAATTAAC

TTCAGCATCCAAGTTTATGAATCGTAGTTAACGTATATTGCTGTTAATATAGTTTAGGAGTAAG

AGTCTTGTTTTTTATTCAGATTGGGAAATCCGTTCTATTTTGTGAATTTGGGACATAATAACAG

CAGTGGAGTAAGTATTTAGAAGTGTGAATTCACCGTGAAATAGGTGAGATAAATTAAAAGATAC

TTAATTCCCGCCTTATGCCTCAGTCTATTCTGTAAAATTTAAAAAATATATATGCATACCTGGA

TTTCCTTGGCTTCGTGAATGTAAGAGAAATTAAATCTGAATAAATAATTCTTTCTGTTAA

SFTPB
>gi|288856298|ref|NM_000542.3| *Homo sapiens* surfactant protein B
(SFTPB), transcript variant 1, mRNA
(SEQ ID NO: 35)

TGTAAATGCTCTTCTGACTAATGCAAACCATGTGTCCATAGAACCAGAAGATTTTTCCAGGGGA

AAAGAGCCCCCACGCCCCGCCCAGCTATAAGGGGCCATGCACCAAGCAGGGTACCCAGGCTGCA

GAGGTGCCATGGCTGAGTCACACCTGCTGCAGTGGCTGCTGCTGCTGCTGCCCACGCTCTGTGG

CCCAGGCACTGCTGCCTGGACCACCTCATCCTTGGCCTGTGCCCAGGGCCCTGAGTTCTGGTGC

CAAAGCCTGGAGCAAGCATTGCAGTGCAGAGCCCTAGGGCATTGCCTACAGGAAGTCTGGGGAC

ATGTGGGAGCCGATGACCTATGCCAAGAGTGTGAGGACATCGTCCACATCCTTAACAAGATGGC

-continued

```
CAAGGAGGCCATTTTCCAGGACACGATGAGGAAGTTCCTGGAGCAGGAGTGCAACGTCCTCCCC

TTGAAGCTGCTCATGCCCCAGTGCAACCAAGTGCTTGACGACTACTTCCCCCTGGTCATCGACT

ACTTCCAGAACCAGACTGACTCAAACGGCATCTGTATGCACCTGGGCCTGTGCAAATCCCGGCA

GCCAGAGCCAGAGCAGGAGCCAGGGATGTCAGACCCCCTGCCCAAACCTCTGCGGGACCCTCTG

CCAGACCCTCTGCTGGACAAGCTCGTCCTCCCTGTGCTGCCCGGGGCCCTCCAGGCGAGGCCTG

GGCCTCACACACAGGATCTCTCCGAGCAGCAATTCCCCATTCCTCTCCCCTATTGCTGGCTCTG

CAGGGCTCTGATCAAGCGGATCCAAGCCATGATTCCCAAGGGTGCGCTAGCTGTGGCAGTGGCC

CAGGTGTGCCGCGTGGTACCTCTGGTGGCGGGCGGCATCTGCCAGTGCCTGGCTGAGCGCTACT

CCGTCATCCTGCTCGACACGCTGCTGGGCCGCATGCTGCCCCAGCTGGTCTGCCGCCTCGTCCT

CCGGTGCTCCATGGATGACAGCGCTGGCCCAAGGTCGCCGACAGGAGAATGGCTGCCGCGAGAC

TCTGAGTGCCACCTCTGCATGTCCGTGACCACCCAGGCCGGGAACAGCAGCGAGCAGGCCATAC

CACAGGCAATGCTCCAGGCCTGTGTTGGCTCCTGGCTGGACAGGGAAAAGTGCAAGCAATTTGT

GGAGCAGCACACGCCCCAGCTGCTGACCCTGGTGCCCAGGGGCTGGGATGCCCACACCACCTGC

CAGGCCCTCGGGGTGTGTGGGACCATGTCCAGCCCTCTCCAGTGTATCCACAGCCCCGACCTTT

GATGAGAACTCAGCTGTCCAGCTGCAAAGGAAAAGCCAAGTGAGACGGGCTCTGGGACCATGGT

GACCAGGCTCTTCCCCTGCTCCCTGGCCCTCGCCAGCTGCCAGGCTGAAAAGAAGCCTCAGCTC

CCACACCGCCCTCCTCACCGCCCTTCCTCGGCAGTCACTTCCACTGGTGGACCACGGGCCCCA

GCCCTGTGTCGGCCTTGTCTGTCTCAGCTCAACCACAGTCTGACACCAGAGCCCACTTCCATCC

TCTCTGGTGTGAGGCACAGCGAGGGCAGCATCTGGAGGAGCTCTGCAGCCTCCACACCTACCAC

GACCTCCCAGGGCTGGGCTCAGGAAAAACCAGCCACTGCTTTACAGGACAGGGGGTTGAAGCTG

AGCCCCGCCTCACACCCACCCCCATGCACTCAAAGATTGGATTTTACAGCTACTTGCAATTCAA

AATTCAGAAGAATAAAAAATGGGAACATACAGAACTCTAAAAGATAGACATCAGAAATTGTTAA

GTTAAGCTTTTTCAAAAAATCAGCAATTCCCCAGCGTAGTCAAGGGTGGACACTGCACGCTCTG

GCATGATGGGATGGCGACCGGGCAAGCTTTCTTCCTCGAGATGCTCTGCTGCTTGAGAGCTATT

GCTTTGTTAAGATATAAAAAGGGGTTTCTTTTTGTCTTTCTGTAAGGTGGACTTCCAGCTTTTG

ATTGAAAGTCCTAGGGTGATTCTATTTCTGCTGTGATTTATCTGCTGAAAGCTCAGCTGGGGTT

GTGCAAGCTAGGGACCCATTCCTGTGTAATACAATGTCTGCACCAATGCTAATAAAGTCCTATT

CTCTTTTATGAGAAAGAAAAAGACACCGTCCTTTAAAGTGCTGCAGTATGGCCAGACGTGGTGG

CTCACACCTGCAATCCCAGCACCTTAGGAGGCCGAGGCAGGAGGATCCTTGAGGTCAGGAGTTC

GAGACCAGCCTCGCCAACATGGTGAAACCCCATTTCTACTAAAAATACAAAAAATTAGCCAAGT

GTGGTGGCATATGCCTGTAATCCCAACTACTCAGAAGGCCGAGGCAGGAGAATTACTTGAACGC

AGGAGAATCACTGCAGCCCAGGAGGCAGAGGTTGCAGTGAGCCGAGATTGCACCACTGCACTCC

AGCCTGGGTGACAGAGCAAGACTCCATCTCAGTAAATAAATAAATAAATAAAAAGCGCTGCAGT

AGCTGTGGCCTCACCCTGAAGTCAGCGGGCCCAGGCCTACCTCACTCTCTCCCTTGGCAGAGAA

GCAGACGTCCATAGCTCCTCTCCCTCACAAGCGCTCCCAGCCTGCCCTCCAGCTGCTGCTCTCC

CCTCCCAGTCTCTACTCACTGGGATGAGGTTAGGTCATGAGGACACCAAAAACCTAAAAATAAA

CAAAAAGCCAAACAAGCCTTAGCTTTTCTTAAAGACTGAAATGCCTGGAAGTGTCCCTTTATTT

ATAAAATAACTTTTGTCATATTTCTTATACATGTTTCTTGTAAGAAATTCAGAAACTACAGACA

AAGAGAGTGGAAATTACCCACTGTCAGGCCTCTGAGCCCAAGCTAAGCCATCATATCCCCTGTG

CCCTGCACGTATACACCCAGATGGCCTGAAGCAACTGAAGATCCACAAAAGAAGTGAAAATAGC

CAGTTCCTGCCTTAACTGATGACATTCCACCATTGTGATTTGTTCCTGCCCCACCCTAACTGAT
```

-continued

CAATTGACCTTGTGACAATACACCTTCCCCACCCTTGAGAAGGTGCTTTGTAATATTCTCCCCA

CCCACCCCACGCCCGCACCCCCGCACCCTTAAGAAGGTATTTTGTAATATTCTCTCCGCCATTG

AGAATGTGCTTTGTAAGATCCACCCCCTGCCCACAAAAAATTGCTCCTAACTCCACCGCCTATC

CCAAACCTACAAGAACTAATGATAATCCCACCACCCTTTGCTGACTCTTTTTGGACTCAGCCCA

CCTGCACCCAGGTGATTAAAAAGCTTTATTGTTCACACAAAGCCTGTTTGGTAGTCTCTTCACA

GGGAAGCATGTGACACCCACAATCCCACCTAGCCCAGGAGAGAGCTACGGCAGGGTGTGTGTTT

TGACACTGAGCTTGGGGCTTTTTCCATCTTCTCCCCACAGCCTCTGGCTCCACACCTCCACCGT

TCAAGCGCCAGAAAGAGCTGTCTATGCAGCCTGCTCTTGGGCCTGGGGATGAGACACACAATTC

ATTGGCTCCTGGATTTTAAGTAGACATTTGTAAATCTATAGCTAACTACTGTCCTTAAAGCCAT

TGTTTCCATTACAAAATCCAACTCTCTGAGAGAAAAGGGTGTTTTAAATTTAAAAAAATAAAAA

CAAGTTTGATTGAGAAAAAAAAAAAAAAA

XAGE-1d
>gi|18157207|emb|AJ318879.1| Homo sapiens mRNA for XAGE-1d
protein
(SEQ ID NO: 36)
GGGAACGCGGCGGAGCTGTGAGCCGGCGACTCGGGTCCCTGAGGTCTGGATTCTTTCTCCGCTA

CTGAGACACGGCGGACACACACAAACACAGAACCACACAGCCAGTCCCAGGAGCCCAGTAATGG

AGAGCCCCAAAAAGAAGAACCAGCAGCTGAAAGTCGGGATCCTACACCTGGGCAGCAGACAGAA

GAAGATCAGGATACAGCTGAGATCCCAGGTGCTGGGAAGGGAAATGCGCGACATGGAAGGTGAT

CTGCAAGAGCTGCATCAGTCAAACACCGGGGATAAATCTGGATTTGGGTTCCGGCGTCAAGGTG

AAGATAATACCTAAAGAGGAACACTGTAAAATGCCAGAAGCAGGTGAAGAGCAACCACAAGTTT

AAATGAAGACAAGCTGAAACAACGCAAGCTGGTTTTATATTAGATATTTGACTTAAACTATCTC

ATAAGTTTTGCAGCTTTCACCAAA

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

What is claimed is:

1. A method of preparing a set of amplified DNAs, the method comprising: a) extracting RNA from a sample from a human subject; b) from the extracted RNA,
  i) reverse transcribing to form marker cDNAs from up to eight marker RNAs, wherein the up to eight marker RNAs comprises GAGE12D, FAM83A, LRGI, and MAGEA4 marker RNAs, wherein GAGE12D marker RNA is reverse transcribed using a first GAGE12D-specific primer hybridized to GAGE12D RNA within a sequence corresponding to SEQ ID NO:32, FAM83A marker RNA is reverse transcribed using a first FAM83A-specific primer hybridized to FAM83A RNA within a sequence corresponding to SEQ ID NO:31, LRG1 marker RNA is reverse transcribed using a first LRG/-specific primer hybridized to LRG1 RNA within a sequence corresponding to SEQ ID NO:33, and MAGEA4 marker RNA is reverse transcribed using a first MAGEA4-specific primer hybridized to MAGEA4 RNA within a sequence corresponding to SEQ ID NO:34;
  ii) amplifying marker DNAs from the marker cDNAs; and
  iii) reverse transcribing to form a reference cDNA from at least one reference RNA; and
  iv) amplifying reference DNA from the reference cDNA, wherein reverse transcribing and amplifying occurs in one or more reaction mixtures comprising: primer oligonucleotides for reverse transcribing each of the up to eight marker RNAs and for amplifying DNAs from the marker cDNAs, wherein the primer oligonucleotides comprise: the first GAGE12D-specific primer and a second GAGE12D-specific primer complementary to SEQ ID NO:32 or its complement; the first FAM83A-specific primer and a second FAM83A-specific primer complementary to SEQ ID NO:31 or its complement; the first LRG1-specific primer and a second LRG1-specific primer complementary to SEQ ID NO:33 or its complement; and the first MAGEA4-specific primer and a second MAGEA4-specific primer complementary to SEQ ID NO:34 or its complement; primer oligonucleotides for reverse transcribing the reference RNA and for amplifying reference DNA from the reference cDNA; reverse transcriptase; and thermostable DNA polymerase.

2. The method of claim 1, wherein the reverse transcribing and amplifying DNAs from marker and reference cDNAs occur in a single reaction mixture.

3. The method of claim 1, wherein amounts of marker and reference DNA amplified from the marker and reference cDNAs are measured in real time during thermal cycling.

4. The method of claim 3, wherein each of the one or more reaction mixtures further comprises: nucleic acid probe oligonucleotides complementary to the marker and reference DNAs amplified from the marker and reference cDNAs.

5. The method of claim 4, wherein the nucleic acid probe oligonucleotides comprise reporter molecules.

6. The method of claim 5, wherein the reporter molecules comprise fluorophores.

7. The method of claim 5, wherein the reporter molecules comprise flap sequences.

8. The method of claim 7, wherein the amounts of marker and reference DNA amplified from marker and reference cDNAs are measured in a PCR-flap assay occurring in the one or more reaction mixtures, wherein each of the one or more reaction mixtures further comprises: FEN-1 endonuclease and one or more FRET cassettes.

9. The method of claim 8, wherein amounts of marker and reference DNA amplified from marker and reference cDNAs are all measured in a single reaction mixture.

10. The method of claim 8, wherein amounts of marker DNA amplified from marker cDNAs are all measured in separate reaction mixtures.

11. The method of claim 10, wherein amounts of marker DNA amplified from marker cDNAs and amount of reference DNA amplified from the at least one reference cDNA are measured in each of the separate reaction mixtures.

12. The method of claim 1, wherein the up to eight marker RNAs is a group of four marker RNAs consisting of GAGE12D, FAM83A, LRG1, and MAGEA4 marker RNAs.

13. The method of claim 1, wherein the up to eight marker RNAs further comprises one or more marker RNAs selected from XAGE-1 d, SETPB, AKAP4, and CYP241 marker RNAs.

14. The method of claim 1, wherein the at least one reference RNA is selected from the group consisting of CASC3 mRNA, β-actin mRNA, U1 snRNA and U6 snRNA.

15. The method of claim 1, wherein the sample is a tissue sample, a blood sample, a serum sample, or a sputum sample.

16. The method of claim 15, wherein the tissue sample comprises lung tissue.

17. The method of claim 1, wherein the reverse transcriptase is MMLV reverse transcriptase.

* * * * *

UNITED STATES PATENT AND TRADEMARK OFFICE
CERTIFICATE OF CORRECTION

PATENT NO. : 11,479,823 B2
APPLICATION NO. : 17/078924
DATED : October 25, 2022
INVENTOR(S) : Hatim T. Allawi et al.

It is certified that error appears in the above-identified patent and that said Letters Patent is hereby corrected as shown below:

In the Claims

Column 71, Claim 1, Line 34 should read:
– RNAs comprises GAGE12D, FAM83A, LRG1, and –

Column 71, Claim 1, Line 44 should read:
– LRG1-specific primer hybridized to LRG1 RNA within –

Column 73, Claim 13, Line 3 should read:
– From XAGE-1 d, SFTPB, AKAP4, and CYP24A1 marker –

Signed and Sealed this
Seventh Day of February, 2023

Katherine Kelly Vidal
*Director of the United States Patent and Trademark Office*